US006498025B1

(12) United States Patent
Miller

(10) Patent No.: US 6,498,025 B1
(45) Date of Patent: *Dec. 24, 2002

(54) METHODS AND COMPOSITIONS FOR CDNA SYNTHESIS

(76) Inventor: Jeffrey E. Miller, 10828 Red Rock Dr., Scripps Ranch, CA (US) 92131

(*) Notice: Subject to any disclaimer, the term of this patent is extended or adjusted under 35 U.S.C. 154(b) by 0 days.

This patent is subject to a terminal disclaimer.

(21) Appl. No.: 08/227,476

(22) Filed: Apr. 14, 1994

Related U.S. Application Data

(63) Continuation of application No. 07/989,851, filed on Dec. 9, 1992, now abandoned.

(51) Int. Cl.[7] .......................... C12Q 1/68; C12P 19/34; C07H 21/02; C07H 21/04
(52) U.S. Cl. ................ 435/91.51; 435/91.2; 435/91.21; 435/5; 435/6; 435/455; 435/471; 435/320.1; 435/252.3; 536/23.1; 536/24.1; 536/24.33; 536/23.5
(58) Field of Search ................ 435/5, 6, 912, 435/91.51, 91.21, 455, 320.1, 252.3; 536/23.1, 24.1, 24.33, 23.5; 935/16.37, 52, 77, 78; 438/471

(56) References Cited

U.S. PATENT DOCUMENTS

| 4,935,372 A | * 6/1990 | Goh | 435/317.1 |
| 4,965,188 A | * 10/1990 | Mullis | 435/6 |
| 5,021,335 A | 6/1991 | Tecott et al. | 435/436 |
| 5,168,038 A | 12/1992 | Tecott et al. | 435/436 |

FOREIGN PATENT DOCUMENTS

EP 0532380 3/1993

OTHER PUBLICATIONS

Barat Nucl Acids Res. (Feb. 1991) 19: 751–757.*
Van Gelder Proc Natl Acad Sci USA (1990) 87: 1663–1667.*
Sambrook et al, Molec Cloning: a Laboratory Manual, 2$^{nd}$ Ed. 1989, cold Spring Harbor Lab Press, NY, p. 17, 4–1.81.*
Kriegler, Gere Transfer and Expression, A Laboratory Manual 1990, Stockton Press, New York, p. 101–102.*
Mogensen Exp Cell Res (1991) 196: 92–98.*
Boehringer Mannher Catalog (1990/1991) p. 70.*
Harada J Biol Chem (1979) 254: 10979–10985.*
Peters J Virol 25: 398–407.*
Van Gelder, R.N., et al. "Amplified RNA Synthesized From Limited Quantities of Heterogeneous cDNA", *Proceedings of the National Academy of Sciences, USA*, vol. 87, pp. 1663–1667, Mar. 1990.
Barat, C. et al. "Interaction of HIV–1 Reverse Transcriptase with a Synthetic Form of its Replication Primer, tRNA$^{lys,3}$", *Nucleic Acids Research*, vol. 19, No. 4, pp. 751–757, Feb. 1991.
Kriegler, M., *Gene Transfer and Expression: A Laboratory Manual*, pp. 101–102, Stockton Press, 1990.
Peters, G. et al, "RNA–directed DNA Synthesis in Moloney Murine Leukemia Virus: Interaction Between the Primer tRNA and the Genomic RNA" *Journal of Virology*, vol. 35, pp. 398–407, Aug. 31, 1979.
Harada, F. et al, "The Primer tRNA for Moloney Murine Leukemia Virus DNA Synthesis: Nucleotide Sequence and Aminoacylation of the tRNA$^{pro}$", *The Journal of Biological Chemistry*, vol. 254, No. 21, pp. 10979–10985, Nov. 10, 1979.
*Reagents for Molecular Biology*, p. 70, Boehringer Mannheim, 1990/1991.
Sambrook, J. et al, "Molecular Cloning: A Laboratory Manual, 2nd Ed." pp. 1.74–1.81 Cold Spring Harbor Laboratory Press, 1989.
Weiss, S. et al., *Gene* 111:183–197 (1992).

* cited by examiner

Primary Examiner—Carla J. Myers
(74) Attorney, Agent, or Firm—James C. Weseman, Esq.; The Law Offices of James C. Weseman

(57) ABSTRACT

Methods and compositions for synthesizing cDNA in vivo are disclosed, wherein a synthetic polynucleotide molecule which anneals in vivo to an RNA template molecule is utilized as a primer for reverse transcriptase in vivo.

69 Claims, 12 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 67 base pairs
       (B) TYPE: nucleic acid
       (C) STRANDEDNESS: single
       (D) TOPOLOGY: unknown (xi) SEQUENCE DESCRIPTION: SEQ ID NO:1:

ACGGATCCTA ATACGACTCA CTATAGGCTC GTTGGTCTAG GGGTATGATT CTCGCTTGGG    60

GTGCGAG    67

(2) INFORMATION FOR SEQ ID NO:2:

(i) SEQUENCE CHARACTERISTICS:
       (A) LENGTH: 66 base pairs
       (B) TYPE: nucleic acid
       (C) STRANDEDNESS: single
       (D) TOPOLOGY: linear (xi) SEQUENCE DESCRIPTION: SEQ ID NO:2:

TGGAATTCTC TTCATGGGGG CTCGTCCGGG ATTTGAACCC GGGACCTCTC GCACCCCAAG    60

CGAGAA    66

(2) INFORMATION FOR SEQ ID NO:3:

(i) SEQUENCE CHARACTERISTICS:
       (A) LENGTH: 68 base pairs
       (B) TYPE: nucleic acid
       (C) STRANDEDNESS: single
       (D) TOPOLOGY: unknown (xi) SEQUENCE DESCRIPTION: SEQ ID NO:3:

ACGGATCCTA ATACGACTCA CTATAGAAAA AAATGGTCTA GGGGTATGAT TCTCGCTTGG    60

GGTGCGAG    68

(2) INFORMATION FOR SEQ ID NO:4:

(i) SEQUENCE CHARACTERISTICS:
       (A) LENGTH: 64 base pairs
       (B) TYPE: nucleic acid
       (C) STRANDEDNESS: single
       (D) TOPOLOGY: unknown (xi) SEQUENCE DESCRIPTION: SEQ ID NO:4:

TGGAATTCTC TTCAAAAAAA AAAAAAAAAA AAAAGAACCC GGGACCTCTC GCACCCCAAG    60

CGAG    64

(2) INFORMATION FOR SEQ ID NO:5:

(i) SEQUENCE CHARACTERISTICS:
       (A) LENGTH: 29 base pairs
       (B) TYPE: nucleic acid
       (C) STRANDEDNESS: single
       (D) TOPOLOGY: unknown (xi) SEQUENCE DESCRIPTION: SEQ ID NO:5:

AAAAAAAAAA AAAAAAAAAA GAACCCGGG    29

(2) INFORMATION FOR SEQ ID NO:6:

(i) SEQUENCE CHARACTERISTICS:
        (A) LENGTH: 59 base pairs
        (B) TYPE: nucleic acid
        (C) STRANDEDNESS: single
        (D) TOPOLOGY: unknown (xi) SEQUENCE DESCRIPTION: SEQ ID NO:6:

```
CGAAGCTTTA AAAAAAAAA AAAAAAAAG AACCCGGGAC CTCTCGCACC CCAAGCGAG        59
```

(2) INFORMATION FOR SEQ ID NO:7:

(i) SEQUENCE CHARACTERISTICS:
        (A) LENGTH: 76 base pairs
        (B) TYPE: nucleic acid
        (C) STRANDEDNESS: single
        (D) TOPOLOGY: unknown (ii) MOLECULE TYPE: RNA (genomic)

(xi) SEQUENCE DESCRIPTION: SEQ ID NO:7:

```
GAAAAAAAUG GUCUAGGGGU AUGAUUCUCG CUUGGGGUGC GAGAGGUCCC GGGUUCUUUU        60

UUUUUUUUUU UUUUUU                                                        76
```

(2) INFORMATION FOR SEQ ID NO:8:

(i) SEQUENCE CHARACTERISTICS:
        (A) LENGTH: 76 base pairs
        (B) TYPE: nucleic acid
        (C) STRANDEDNESS: single
        (D) TOPOLOGY: unknown (xi) SEQUENCE DESCRIPTION: SEQ ID NO:8:

```
GAAAAAAATG GTCTAGGGGT ATGATTCTCG CTTGGGGTGC GAGAGGTCCC GGGTTCTTTT        60

TTTTTTTTTT TTTTTT                                                        76
```

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (xi) SEQUENCE DESCRIPTION: SEQ ID NO:9:

```
CTGTTGCAAC TCACAGTCTG GAACCCGGGA CCTCTCGCAC CCC                          43
```

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (xi) SEQUENCE DESCRIPTION: SEQ ID NO:10:

```
GGGGAGTGGC GAGCCCTCTT GAACCCGGGA CCTCTCGCAC CCC                          43
```

METHODS AND COMPOSITIONS FOR CDNA SYNTHESIS

This is a continuation of Application Ser. No. 07/989,851, filed Dec. 9, 1992 now abandoned.

TECHNICAL FIELD

The present invention relates to methods and compositions for DNA synthesis, and, more particularly, for the synthesis of complementary DNA in vivo.

BACKGROUND OF THE INVENTION

The present invention is a tool for molecular biology. An introduction to the nomenclature of molecular biology, the structure of DNA, RNA and proteins and the interrelationships between these molecules, is provided in Chapter 4, *Synthesis of Proteins and Nucleic Acids* of Darnell et al., *Molecular Cell Biology*, Scientific American Books (1989). A more detailed treatment of these issues is set forth in the full text of Darnell et al., (1989) and in Lewin, *Genes IV*, Oxford University Press (1990).

Hereditary information is encoded in the genes of an organism. Genes are made of polymers of nucleic acids, usually deoxyribonucleic acid (DNA). DNA is composed of a series of four nucleotide bases; the hereditary information carried by a gene is encoded by the specific sequence of nucleotide bases in the DNA molecule. The genetic information within structural genes encodes proteins; the sequence and structure (and therefore function) of a particular protein is determined by the order of the nucleotide bases within the gene that encodes that protein. Proteins determine an organism's identity; from cellular structures to the organism's response to its environment. Thus, the genes that encode these proteins determine an organism's identity.

The information encoded within a structural gene is "expressed" by a cell through the processes of transcription and translation. Transcription results in the production of an intermediate carrier of the genetic code, termed messenger RNA (mRNA). Messenger RNA is effectively a copy of the gene; it is a polymer of ribonucleic acid (hence "RNA") rather than of deoxyribonucleic acid.

In eukaryotic organisms (which are generally more complex organisms than bacteria), genes are made up of coding regions (termed "exons") and non-coding regions (termed "introns"). Exons directly encode the protein sequence of the gene. Introns may be very large and there may be a large number of intron sequences within a particular gene. The role of the non-coding intron sequences is unclear. However, there is evidence that these intervening sequences serve two critical purposes: first they divide the exon coding regions into smaller protein coding units and so minimize the chances of errors during transcription and translation; second, they relegate discrete portions or cassettes of protein sequence to exon units which can be more easily shuffled during the course of evolution and therefore facilitate the development of new proteins which may ultimately enhance the survival of the species.

The transcription process involves the formation of an mRNA copy of the entire gene. That is, the mRNA produced by the transcription process contains a copy of both the non-coding intron sequences and the protein-encoding exon sequences. Thus the mRNA first produced by transcription is the same length as the gene from which it was copied. Subsequently, this immature mRNA undergoes a processing stage during which the non-coding intron sequences are spliced out. The resulting processed mRNA molecules thus contain only the information required to encode the protein (i.e. they contain copies of only the joined exon sequences). These processed mRNA molecules are thus considerably shorter in length than the "genomic sequence" (the gene exons and introns as they exist in the chromosome) from which the mRNA was initially copied. The processed mRNA is also modified at this stage to include a polyriboadenylic acid, poly(A), tail at one end of the molecule (the 3' end) and a "cap" structure at the other end of the molecule (the 5' end) (standard nomenclature assigns one end of DNA and RNA molecules as the 5' end and the other as the 3' end, according to the terminal chemical groupings of the molecule). An mRNA molecule that has been processed to remove introns and has a 5' cap and a 3' poly(A) tail is termed a "mature" mRNA molecule. A greatly simplified diagram of the transcription process, illustrating removal of the non-coding intron sequences is shown in FIG. 1.

The step of converting the information carried by the mature messenger RNA into a protein is termed translation. Translation is the final step of the means by which the information encoded by the nucleotide sequence within a structural gene is converted into a specific protein composed of a sequence of amino acids.

The cloning of genes became possible in the 1970's. In early experiments, small genes were cloned from bacteria. Since that time advances in molecular biology and genetic engineering have developed at an extraordinary rate, such that the sequence of the entire human genome is now being determined. Despite rapid advances in the technology of this field, a number of limitations are still apparent. One of these is the difficulty of cloning very large structural genes.

The size of a gene is measured in the number of nucleotide bases that it contains, usually expressed in terms of thousands of bases (kilobases or Kb). Although there are several examples of larger genes, the total coding sequence of most structural genes (the exons) typically totals 1–10 Kb. However, the presence of multiple large intron sequences between the exon segments means that at the genomic level these genes are spread out over a much larger area, frequently spanning tens or even hundreds of kilobases. Present gene cloning vectors such as YACs (Yeast Artificial Chromosomes) allow the cloning of very large (100–300 Kb) genomic segments; however, these genomic inserts include the noncoding intron sequences, which precludes the expression of protein in an artificial system. A partial genetic sequence, or sequence containing introns, results in the expression of a nonfunctional, truncated protein, or, when the sequence for the 5' translation start site is missing, results in expression of a unrelated garbled protein sequence. Even if a partial gene may be identified through a screening process, it is then necessary to recover the remaining portions of the gene. This can be an extremely complicated process. If the gene contains many intron sequences, and is thus large, years of effort can be expended in attempting to recover the remaining pieces of the gene. Additional effort may then be required to determine the relative order of the gene fragments and to distinguish exon from intron sequences. The ability to clone a gene as a contiguous protein coding cassette is particularly important where identification of the gene is achieved by means of a detection technique which relies on production of the protein in a recombinant bacterial or viral system and "screening" for the function or structure of the desired protein—a common technique of detecting cloned genes.

To clone structural genes, molecular biologists have taken advantage of the cellular mRNA processing function described above whereby intron sequences are spliced out of the immature mRNA to produce a mature mRNA that is considerably smaller that the original gene. By converting the mature mRNA molecule back into a DNA molecule (hence the term, "reverse transcription"), one can obtain the original coding sequence (the exons) without the extraneous intron sequences. Such a DNA molecule is termed a complementary DNA because it is complementary to the mRNA molecule from which it was derived. Complementary DNA (cDNA) synthesis is the preferred technique for gene cloning because it results in the recovery of the desired gene in a relatively small, contiguous protein coding cassette amenable to recombinant protein production.

An additional and important use of cDNA technology is to identify those genes that are being expressed by a cell at a particular time. Gene expression requires substantial energy expenditure on the part of the cell, and mRNA molecules are designed to be short-lived "protein requests"; therefore, with a few exceptions (notably in the egg during development), only those genes that code for proteins which are immediately needed are transcribed into mRNA. By making cDNA copies of the existing mRNA population in a cell, and cloning the cDNAs produced, researchers are able to produce a cDNA library from the genes which were being expressed at that time. Researchers can thus determine specifically which genes are expressed in a given tissue type, at a given stage of development, or in response to an applied stimulus.

Complementary DNA clones are extremely important in both research and industry. Research requires expression of the cloned gene in order to determine the protein's function and structure. In addition, large amounts of protein are required for the production of polyclonal or monoclonal antibodies which are indispensable for following small amounts of the protein through research protocols, and in determining the location of the protein in the cell. Bacteria are commonly used as hosts in which a cloned gene is expressed. The genes of prokaryotes, including bacteria, do not contain introns, and so these cells do not have the splicing machinery necessary to process immature mRNA into a mature mRNA that can be translated into a functional protein. Genomic clones of eukaryotic genes (i.e., containing introns and exons) can not be expressed in a bacterial host, whereas a cDNA copy of the same gene can be expressed—either in procaryotes or eukaryotes. Thus, cDNA clones are routinely used for large scale protein production. This artificial protein expression is termed "recombinant protein" production and is an increasingly common way of producing many of the pharmaceuticals which for years were accessible in small amounts by tedious extraction from other animal's tissues.

Techniques presently used for cDNA synthesis are reviewed in Berger and Kimmel, *Guide to Molecular Cloning Techniques* in *Methods in Enzymology* Volume 152, Academic Press Inc. (1987), in Sambrook et al., *Molecular Cloning*, Cold Spring Harbor Laboratory Press (1989), and in Okayama, H., et al., *Meth. Enzymol.* 159:3–27 (1987). A review of mRNA isolation techniques is presented in Chapters 7 and 8 of Sambrook et al. (1989).

Isolation of mRNA is a long, tedious process with a number of technically difficult steps. In summary, a typical procedure for isolating mRNA from a cell requires (1) disruption of cells to release cellular contents, (2) isolation of total RNA from the cell, (3) selection of the mRNA population by running the extracted RNA through an oligo (dT) cellulose column and (4) size fractionation of the isolated mRNA. At all stages, great care is required to ensure that the preparation does not come into contact with active ribonuclease enzymes which can destroy the RNA. Because the goal of the cDNA cloning procedure is to obtain "full length" cDNA clones that contain the entire coding sequence of the gene, it is extremely important to use procedures that maintain the integrity of the mRNA. Ribonuclease (RNAse) enzymes are very stable and so even a very small amount of the active enzyme in an mRNA preparation will cause problems. RNAse is present on virtually all surfaces, including human skin, and is thus very easily introduced into the RNA preparation. To avoid contamination problems, all solutions, glassware and plasticware must be specially treated. The cells from which the mRNA is to be isolated are disrupted in solutions which are extremely harsh and contain components which immediately inactivate the omnipresent ribonuclease enzymes; all subsequent solutions used in RNA preparation are treated with diethylpyrocarbonate (DEPC), a suspected carcinogen) which inactivates RNAse. Often a laboratory will set aside particular equipment and work space that is designated to be "ribonuclease free". The potential for RNA degradation starts at the first step of breaking open the cells (the cells themselves contain ribonucleases which, upon lysis of the cells, come into contact with the RNA), and continue throughout the procedure.

Total RNA extracted from a cell is made up of messenger RNA (mRNA), transfer RNA (tRNA) and ribosomal RNA (rRNA). The mRNA typically makes up only 1–3% of the total cellular RNA (approximately $1\times10^{-12}$ g mRNA per eukaryotic cell, Sargent, T. D., Methods Enzymol. 152:423–432 (1987)). Most cDNA synthesis reactions rely on the presence of the poly(A) tail present only in mature mRNA transcripts. The mature RNA transcripts are selectively extracted from the bulk of the cellular RNA, usually by affinity chromatography. This is an essential step for successful in vitro cDNA synthesis; failure to enrich for the mature mRNA will result in a low yield of poor quality cDNA.

As a final stage prior to cDNA synthesis, the mRNA preparation may be size selected. This is usually performed to remove the smaller size molecules (usually degraded forms of larger mRNAs) which would otherwise interfere with the cDNA cloning procedure. Size selection may also be performed to enrich for an mRNA species of known size. Size selection may be performed by electrophoresis through agarose gels, by column chromatography, or by sedimentation through sucrose gradients. These techniques result in lower yields, and may require the presence of methylmercuric hydroxide to disrupt secondary intramolecular structure. Methylmercuric hydroxide is extremely toxic and volatile, and requires great care in handling. Safer alternatives (such as the use of gels containing glyoxal/dimethyl sulfoxide or formaldehyde) are available, but these techniques also involve dangerous chemicals and have associated disadvantages.

Additional disadvantages arise from the necessity of extracting mRNA from cells prior to cDNA synthesis. For example, cDNA cloning is often used to assess which genes are expressed in a cell under particular conditions or at a particular stage in the development of the organism. The time and conditions required to extract the mRNA may themselves produce alterations in the gene expression pattern of the cell. Furthermore, mRNA molecules which are present in very low abundance (estimated at 20 copies per cell) or which are unstable may be lost during the RNA isolation procedure. There is currently a lower limit on the number of cells necessary to produce a cDNA library due to the inherent losses incurred in mRNA isolation procedures. This invention addresses this problem by completely circumventing the initial mRNA isolation requirement.

Following extraction and purification of the mRNA, cDNA synthesis is performed in vitro. All methodologies presently used for cDNA synthesis follow mRNA extraction and purification, or are performed on dead cells under in vitro conditions. These methodologies are reviewed in detail in Kimmel and Berger (1987); Okayama, H., et al., (1987); and Embleton, M. J., et al., *Nucleic Acids Res.* 20:3831–3837 (1992)).

All of the presently available techniques utilize RNA-dependent DNA polymerase enzymes (more commonly termed reverse transcriptase enzymes) to synthesize the first strand of the cDNA from the mRNA template. Reverse transcriptase, like other DNA polymerases, cannot initiate nucleic acid synthesis de novo. Rather, it adds the first nucleotide of the nascent cDNA strand to the hydroxyl group at the 3' end of a preexisting RNA or DNA strand that is annealed to the mRNA template. This preexisting strand to which the enzyme adds the first nucleotide is called a primer and appears to be absolutely required for reverse transcriptase activity. In their natural role, reverse transcriptase enzymes enter the cell within the infecting retrovirus. The enzyme is already associated with both a specific cellular transfer RNA (tRNA) molecule (present in all host cells), which the virus scavenged from a host cell during the previous infection, and a viral RNA chromosome. Transfer RNA molecules are short (70 to 80 nucleotides long) RNA molecules which are folded into complex three-dimensional structures; their usual cellular role is in the translation process (Darnell et al. (1989), chapter 4). After the virus enters a newly infected cell the reverse transcriptase-tRNA complex acts as primer for an in vivo (in the cell) reverse transcriptase reaction, using the viral RNA molecule, to which this complex is already bound, as the RNA template. The cDNA made from this in vivo reaction is then converted to double-stranded DNA by the same reverse transcriptase enzyme complex, and integrated into a chromosome of the infected cell. It is important to note that the reverse transcriptase-tRNA primer complex necessary for viral replication will not act as a primer for cDNA synthesis from cellular mRNA templates because the tRNA species (2 of about 40 types present in the cell) which have affinity for the reverse transcriptase enzyme are complementary to, and will therefore only prime from, sequences present on specific RNA molecules. It is interesting to note, however, that there are viruslike 30S (VL30) elements present in mouse cells which have regions of strong homology to retroviruses. These elements have properties of defective type C viruses, are reverse transcribed and are packaged into retroviral virions (Howk, R. S., et al., *J. Virol.* 25:115–123 (1978); Besmer, P. U., et al., *J. Virol.* 29:1168–1176 (1979)).

When reverse transcriptase enzymes are utilized for in vitro (outside the cellular environment) cDNA synthesis, the requirement of the enzyme for a primer molecule is usually satisfied by the inclusion of a oligodeoxynucleotide primer (s) in the reaction mixture. Most commonly, the primer is an oligomer of deoxyribothymidylic acid, oligo(dT). This primer is complementary to the poly(A) tail located at the 3' and of the mRNA molecule ("A" nucleotides are complementary to, an anneal to "T" or "U" nucleotides). Thus, this oligo(dT) primer molecule anneals to the poly(A) tail region and serves as a primer for the reverse transcriptase enzyme. Alternatively, in vitro cDNA synthesis may utilize an oligonucleotide primer that is complementary to other sequences within the RNA molecule; however, because of the extensive stretch of complementary nucleotides necessary for annealing to occur, such a primer will be "sequence specific" for the mRNA molecule to which it is designed to anneal. Synthesis of such a sequence specific primer requires prior knowledge of the nucleotide sequence of part of the mRNA. The primer requirements of reverse transcriptase enzymes are discussed in Chapter 5 of Sambrook, et al. (1989).

The product of the initial reverse transcriptase reaction in vitro is a single-stranded complementary DNA copy of the mRNA molecule. This reaction is often referred to as "first strand cDNA synthesis." Thereafter, various techniques are used to generate the second strand of the cDNA. The resultant double-stranded DNA (dsDNA) molecules are then modified at the ends, and inserted into a "vector" which allows growth, selection, and amplification of each copy. Most commonly used techniques (eg. Okayama and Berg, *Molecular and Cellular Biology* 2:161–170 (1982)) may be summarized as follows: Following extraction and purification of the mRNA and in vitro reverse transcription of the mRNA to produce single-stranded cDNA molecules, the mRNA template is eliminated to allow synthesis of the second strand of DNA and thereby form a double-stranded cDNA molecule; specific DNA linkers are then attached to the blunted end of the double-stranded cDNA, and the cDNA is ligated into a suitable cloning vector.

In all presently used techniques, the reverse transcriptase-catalyzed step of making a cDNA copy of the mRNA is always performed under in vitro conditions. The quality of the cDNA synthesis (that is, the ability to generate both accurate and full-length complementary DNA) depends upon the fidelity and the processivity of the enzyme chosen, and the conditions under which the reaction is performed. Clearly less than full-length cDNA is not acceptable, and a high error rate will compromise the utility of the cDNA produced. The use of the reverse transcriptase in vitro, rather than under the in vivo conditions which the enzyme has evolved to function, appears to adversely affect both the fidelity and processivity of the enzyme. The in vitro fidelity of MuLV reverse transcriptase has been estimated to be $10^{-4}$ (i.e. one wrong nucleotide per 10,000 bases or 10 errors per 100 kb), and recent studies have determined that the in vivo fidelity is approximately $2 \times 10^{-5}$ (1 error for every 50,000 bases copied, 2 errors per 100 kb; Mont et al., *J. Virol.* 66:3683–3689 (1992)). In addition, it is difficult to obtain full length first strand synthesis in an artificial environment whereas the processivity of the enzyme in the in vivo cDNA synthesis reactions is excellent; with cDNA incorporation extending well past the 10 kb range (see included data). While conditions have been developed to optimize the performance of reverse transcriptase enzymes in vitro, these conditions do lead to a certain frequency of errors, and premature termination of first strand cDNA synthesis. It is clear that the in vitro conditions do not reflect the optimal conditions for the enzyme.

Thus, present techniques for cDNA synthesis are limited by (1) the requirement that the mRNA be extracted and purified from cells and (2) the performance of the reverse transcriptase enzyme under in vitro conditions. In combination, these factors limit: the ease of cDNA synthesis; the efficiency of cDNA synthesis; the size of cDNA molecules that can be produced (thereby the genes that are readily clonable by this technique); the accuracy of cDNA synthesis in determining which genes are expressed under particular conditions; and the fidelity of the cDNA produced.

It is an object of the present invention to provide a technique of cDNA synthesis that does not require the isolation of mRNA molecules from cells.

It is a further object of the present invention to provide a technique of cDNA synthesis that does not require in vitro activity of reverse transcriptase.

It is an additional object of the present invention to provide a technique of cDNA synthesis wherein the efficiency of the technique, the fidelity of the cDNA produced and the size of cDNA that the technique is capable of producing are superior to all presently used techniques.

DISCLOSURE OF THE INVENTION

The present invention relates to methods and compositions for the synthesis of complementary DNA copies of RNA templates in vivo.

In accordance with the present invention, a method for synthesizing a complementary DNA copy of an RNA template molecule is provided. The method comprises providing a polynucleotide molecule which is capable of annealing in vivo to an RNA template molecule, providing at least one reverse transcriptase enzyme which is capable of initiating DNA synthesis using the polynucleotide molecule as a primer, introducing the polynucleotide molecule into a viable target cell in the presence of the reverse transcriptase enzyme and incubating the target cell under conditions which permit the synthesis of a DNA molecule complementary to the RNA template molecule.

A further aspect of the invention provides a method for producing in vivo a complementary DNA copy of an RNA template molecule of which at least a partial sequence is known. This method comprises providing a DNA molecule comprising a sequence which encodes a promoter operatively linked to a sequence which encodes a polynucleotide molecule which is capable of annealing in vivo to an RNA template molecule and further capable of functioning as a primer for at least one reverse transcriptase enzyme; providing a first nucleotide primer wherein said primer is homologous to a sequence located 5' to the end of the promoter sequence, and providing a second nucleotide primer wherein said primer comprises a 3' sequence that is complementary to a 3' region of the polynucleotide molecule joined to a 5' sequence that is complementary to a portion of the known RNA template molecule sequence. Thereafter, the DNA molecule is contacted with the first and second primers, and the mixture is then treated under conditions and with reagents suitable for amplifying the cloned DNA molecule. At least one amplified DNA molecule produced thereby is then treated under conditions and with reagents suitable for production of an encoded RNA molecule, which is introduced into a viable target cell in the presence of at least one reverse transcriptase enzyme which is capable of initiating DNA synthesis using said RNA molecule as a primer. The target cell is then incubated under conditions such that a DNA molecule complementary to at least one RNA template molecule is produced.

Also provided in accordance with the present invention are compositions useful in the practice of the present method. Such compositions include polynucleotide molecules which are capable of annealing in vivo to an RNA template molecule and further capable of functioning as primer molecules for at least one reverse transcriptase enzyme, together with DNA molecules and recombinant DNA vectors encoding such polynucleotide molecules, and kits containing such compositions.

BRIEF DESCRIPTION OF THE DRAWINGS

FIG. 2 depicts the cloning of gene cassettes in the present invention, in which

FIG. 3 depicts the relationships involved in reverse transcriptase, tRNA primer, and RNA template interactions necessary for cDNA synthesis, in which

DETAILED DESCRIPTION OF THE INVENTION

Figure 1:
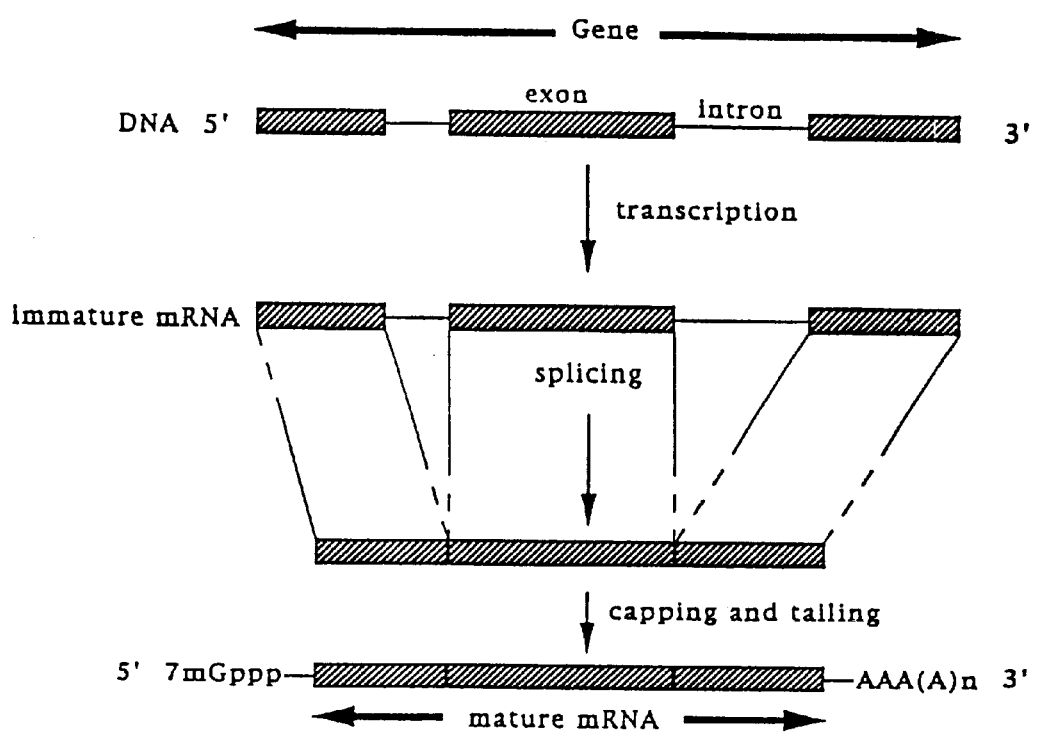
FIG. 1 depicts a simplified diagram of the eukaryotic RNA transcription process, illustrating removal of the non-coding intron sequences during mRNA processing.

The present invention relates to methods and compositions for the synthesis of complementary DNA (cDNA). This invention provides, for the first time, a method by which in vivo cDNA synthesis is made possible. In this method, a suitable primer molecule is introduced into a viable target cell in the presence of a reverse transcriptase enzyme, and the target cell is incubated under conditions such that a DNA molecule complementary to an RNA template molecule is produced. In certain embodiments of the invention, the RNA template molecule is messenger RNA (mRNA), and in many embodiments, the polynucleotide molecule is a modified reverse transcriptase-cognate primer transfer RNA molecule.

Unless otherwise defined, all technical and scientific terms will be used in accordance with the common understanding of persons ordinarily skilled in the art to which the present invention is related. As used herein, the following terms shall have the assigned meanings unless a contrary definition is clearly indicated from the context in which the term is used.

The term template indicates a nucleotide sequence from which a complementary sequence is produced.

The term analog is used to indicate any sequence-specific representative of a naturally-occurring nucleotide.

The term reverse transcriptase enzyme is taken to mean any polymerase which can catalyze the addition of a deoxynucleotide triphosphate or analog thereof to a primer annealed to an RNA template.

The term polynucleotide includes homo- and heteropolymers of deoxyribonucleic acids, ribonucleic acids and analogs thereof.

The term modified reverse transcriptase-cognate primer transfer RNA molecule refers to any tRNA molecule, whether produced chemically, by means of an artificial biological system, or purified from a biological source, which is modified so as to prime the activity of a specific reverse transcriptase enzyme in vivo.

The term expression cassette refers to a DNA construct which includes all sequences necessary for the expression of the coded product. Accordingly, an expression cassette will include DNA encoding at least a promoter region, the sequence of interest and a transcription termination region.

The terms vector and plasmid are interchangeably used to include any means which permits DNA to be replicated and selected in a particular system.

The term operative linkage refers to nucleotides which are joined in a manner which preserves the functional relationship between the sequences on each side of the linkage. For example, a promoter operatively linked to a DNA sequence will be upstream both with respect to the direction of transcription and with respect to the transcription initiation site and inserted in a manner such that transcription elongation proceeds through the DNA sequence.

The present method of cDNA synthesis does not require the isolation of mRNA from cells. Because in vivo cDNA synthesis eliminates the problems associated with conventional in vitro techniques where mRNA isolation is required (or the cells are killed and subjected to harsh conditions), the mRNA templates are more likely to be intact, and full length cDNA clones can be more reliably obtained. Furthermore, in vivo cDNA synthesis does not require the in vitro activity of reverse transcriptase, but rather permits the reverse transcription step to be performed in vivo (i.e. within the cellular environment), such that the efficiency, fidelity and processivity of the reverse transcriptase enzyme is optimized. Thus, longer cDNA clones, with few nucleotide sequence errors may be produced by this method. In addition, it is easier to perform, requires a considerably shorter period of time, and the procedure can potentially provide cDNA product starting with a smaller number of initial cells.

As described in the background of the invention section above, conventional cDNA synthesis requires isolation and purification of mRNA from cells, followed by an in vitro cDNA synthesis step. In the in vitro cDNA synthesis step, the requirement for a primer for the reverse transcriptase enzyme is most commonly met by supplying an oligo(dT) primer molecule that anneals to the poly(A) tail of mRNA molecules, or an oligonucleotide molecule that is complementary to a known portion of target mRNA sequence. However, neither of these types of oligonucleotide primers are effective in vivo (see Examples below). Although specific evidence is lacking to confirm why simple polynucleotide oligomers of complementary sequence which successfully prime in vitro cDNA synthesis reactions fail to prime in vivo cDNA synthesis reactions, there are at least two (2) possible explanations to ascribe for the failure: 1) the reverse transcriptase enzyme is known to recognize and associate with cognate tRNA molecules which have a specific sequence and, therefore, three dimensional structure. This has been studied in detail with both natural and synthetic tRNA molecules by means of gel mobility shift experiments with the reverse transcriptase enzyme from HIV (Barat, C., et al., *EMBO J.* 8:3279–3285 (1989); Barat, C., et al., *Nucleic Acids Res.* 19:751–757 (1991); Weiss, S., et al., *Gene* 111:183–197 (1992)). Simple oligomer primers do not contain this structural requirement, and so, the reverse transcriptase enzyme may not recognize and associate with the primer under in vivo conditions, even if the polynucleotide primer is able to anneal to the mRNA template. 2) Alternatively, the polynucleotide primer which anneals to the template under in vitro conditions, simply may be unable to anneal to an mRNA template in vivo.

In the natural life-cycle of retroviruses, viral reverse transcriptase enzymes utilize host tRNA molecules as primers in order to synthesize a DNA copy of the single-stranded retroviral RNA genome. There may be more than 40 different types of tRNAs in animal cells. Each infective retrovirus particle contains two copies of a single-stranded viral RNA chromosome each of which is associated with a specific host tRNA molecule which anneals to a particular region of the retroviral RNA termed the primer binding site. To initiate the reverse transcription process, a sequence of bases at the 3' end of the tRNA anneals to the primer binding site of the retroviral RNA. The reverse transcriptase enzyme (which is already associated with this complex) then utilizes this tRNA as a primer molecule, adding the first nucleotide of the nascent DNA molecule to the 3' hydroxy terminal of the tRNA.

The specificity of priming retroviral reverse transcription is determined by the base pair sequence at the 3' end of the tRNA molecule which anneals to the retroviral genome. Each retrovirus utilizes a tRNA primer capable of annealing to the specific primer binding site sequence present in the retrovirus genome. For example, the human immunodeficiency virus (HIV) genome utilizes tRNA$_3^{Lys}$ as a primer. To initiate synthesis of a DNA copy of the HIV virus, eighteen nucleotides at the 3' end of the tRNA$_3^{Lys}$ unfold and base pair with the HIV primer binding site (Weiss et al., *RNA Tumor Viruses*, Cold Spring Harbor (1982); Goff, *J. Acquired Immune Deficiency Syndrome* 3:817–831 (1990)). Thus, the eighteen nucleotides at the 3' terminal of the tRNA$_3^{Lys}$ are complementary to the HIV primer binding site sequence. In addition to this annealing of the tRNA primer to the viral RNA template, portion(s) of the same tRNA molecule will be recognized by the viral reverse transcriptase enzyme so that a trimolecular complex is ultimately formed (tRNA primer-reverse transcriptase-RNA template).

Therefore, for all in vivo cDNA synthesis reactions, a primer molecule should fulfill two criteria. Firstly, the primer molecule should be able to anneal in vivo to a target RNA molecule; secondly, the annealed primer-RNA complex will be utilized by a reverse transcriptase enzyme such that the enzyme can catalyze cDNA synthesis using the RNA template and the annealed primer. The oligonucleotide primers presently used for in vitro cDNA synthesis do not function in vivo (see data, included). Furthermore, while specific tRNA molecules are able to function as primers for the in vivo action of reverse transcriptase on the retroviral genome, these tRNA primers anneal specifically to the retroviral primer binding site and are not designed to anneal to sequences present in all mature cellular mRNA molecules. The present invention provides a method of in vivo cDNA synthesis by providing primer molecules that anneal to all polyadenylated cellular mRNA molecules, and are utilized by the reverse transcriptase enzyme such that a cDNA copy of the mRNA molecule to which the primer molecule is annealed is produced. This invention mimics the retroviral replication process (actually an in vivo cDNA synthesis reaction) substituting a modified tRNA primer for the naturally occurring cellular tRNA primer.

In an embodiment of the present invention, the primer molecule is a modified reverse transcriptase-cognate primer tRNA molecule wherein the 3' region of the tRNA molecule (that portion which anneals to the viral RNA primer binding site and serves to prime retroviral reverse transcription) is replaced with a polyuridylic acid sequence such that the tRNA molecule anneals to the 3' poly(A) tail that is present on mature cellular mRNA molecules. Such a preferred tRNA primer (a "polyu tRNA primer") may be used to synthesize in vivo cDNA copies of all mature mRNA molecules contained within a viable cell. Because this primer will anneal to all mature mRNA molecules, the primer may be used to produce a cDNA library, that is a collection of cDNA molecules that represents all of the structural genes being expressed in the cell at that given point in time.

In another embodiment of the present invention, the 3' region of the tRNA primer is modified so that it is complementary to part of a specific RNA sequence. This requires that either the nucleotide sequence of a desired RNA molecule is already known, or that one wishes to produce cDNA from a population of RNA which contains that complementary sequence. Synthesis of specific cDNA molecules may be useful in many different ways, including, but not limited to the following: A sequence-specific tRNA primer may be utilized to clone cDNAs with known sequence, or from genes which represent a specific gene family (all of which share a common sequence). Alternatively, a primer which is selective for an RNA template can be used for in vivo DNA sequencing reactions to determine the 5' sequence of a desired RNA template, without the need to clone and isolate the template. In addition, where the expression of a particular mRNA species is a reliable indicator of a particular disease condition, in vivo cDNA synthesis may be a useful alternative to polymerase chain reaction (PCR) based diagnostic techniques, or could be utilized as a therapeutic agent in conjunction with such diagnostic techniques. For example, an HIV-specific complementary primer could incorporate modified deoxynucleotide bases into a cDNA which could be used for detection, sequencing or sorting (Link, H, et al., *J. Med. Virol.* 37:143–148 (1992); Prober, J. M. et al. (1989)), or the bases could be designed such that the incorporated nucleotide analogs could be made cytotoxic, so that only infected CD4 cells would be eliminated, leaving uninfected CD4 cells viable). In addition, a sequence-specific tRNA primer could be used to take an internal (in vivo) "snapshot" of the transcription pattern present in a cell or tissue to determine the relative ratio of splice-variants or gene family transcripts during a specific period of development or induction. Polymerase chain reaction (PCR) has been used for this purpose in the past and is, at best, unreliable and biased due to problems which occur during amplification (Gilliland, G., et al. in: *PCR Protocols: A Guide to Methods and Applications*, Academic Press (1990)).

Thus, the present invention includes primer molecules that may be used for in vivo cDNA synthesis. More specifically and in preferred embodiments, these primer molecules are modified reverse transcriptase-cognate primer transfer RNA molecules. Typically, modification of the tRNA nucleotide sequence at the 3' end will involve replacement of an equivalent number of tRNA bases such that the substituted bases form a sequence complementary to the target RNA molecule. In preferred embodiments of the present invention, bases at the 3' end of the tRNA molecule are substituted with a replacement sequence. In another preferred embodiment of the present invention, 20 nucleotide bases at the 3' end of the Molony murine leukemia virus reverse transcriptase tRNA$^{Pro}$GGG cognate primer are substituted with uracil residues.

The three dimensional structure of a tRNA molecule is thought to be important in the recognition of the tRNA molecule by reverse transcriptase. Transfer RNA molecules in solution are folded into a three dimensional structure the backbone of which is a stem-loop structure resembling a cloverleaf. The four stems of this cloverleaf are stabilized by Watson-Crick base pairing (three of the four stems end in loops). As an integral part of the structure of tRNA molecules, the bases at the 3' end of the tRNA form base paired bonds with the base at the 5' end of the tRNA. A simplified primary structure of a tRNA molecule is shown in FIG. 2B. Modifications of the sequence of nucleotide bases at the 3' end of the tRNA molecule as described above may disrupt the base pairing interactions of the 3' and 5' ends of the tRNA molecule and may therefore disturb the overall three dimensional structure of a tRNA molecule. In order to minimize the disruption of the structure caused by these modifications, other modifications of the tRNA sequence may be required.

In certain embodiments of the present invention, compensatory nucleotide base changes are made to the region of the 5' end of the tRNA molecule such that the modified 5' and 3' ends of the molecule are able to form Watson-Crick base pairs. In addition, an extra guanine residue was added to the 5' end of the coding sequence to facilitate in vitro production of the tRNA primer utilizing T7 RNA polymerase. It will be apparent to one skilled in the art that the particular compensatory nucleotide base changes made at the 5' end of the molecule will depend upon the substitutions made at the 3' end of the molecule. For example, where the 3' end of the tRNA molecule is modified to a polyuridylic acid sequence (in a polyu tRNA primer), the substitution of the existing bases at the 5' end of the tRNA molecule with adenine bases will serve to restore the Watson-Crick base pairing in this region of the molecule and thus preserve the three dimensional structure of the tRNA.

One skilled in the art will recognize that the practice of this invention does not require that the primer molecule used for in vivo cDNA synthesis is derived from a preexisting tRNA molecule. Thus, any oligonucleotide that is capable of (a) binding in vivo to an RNA molecule and (b) acting as a primer for a reverse transcriptase enzyme such that synthesis of a DNA molecule complementary to that RNA template molecule can occur, can be utilized in the in vivo cDNA synthesis method of the present invention. The suitability of a particular primer for use in in vivo cDNA synthesis may be assessed by performing in vivo cDNA synthesis as described below and assaying the products of that synthesis.

Each of the retroviruses produces a reverse transcriptase enzyme which uses specific cognate tRNA primers encoded and derived from their host cell for priming and initiating cDNA synthesis during their replication cycle. For example, the reverse transcriptase from human immunodeficiency virus (HIV) utilizes $tRNA_3^{Lys}$ as a primer; the Moloney murine leukemia virus (MoMuLV) reverse transcriptase utilizes $tRNA_{1,2}^{Pro}$ for priming, and the Rous sarcoma virus (RSV) utilizes $tRNA^{Trp}$ for priming. In these combinations, the viral reverse transcriptase enzyme-cellular tRNA molecules are associated and form detectable complexes. Therefore, when the unique 3' nucleotide sequence of the tRNA primer molecule anneals to the complementary bases of the viral RNA template, it actually brings the reverse transcriptase enzyme to the template to form the trimolecular complex utilized for the initiation of cDNA synthesis. This facilitation of enzyme, primer, template association is an indispensable step in viral replication and is mimicked in this invention. There is evidence that there is some flexibility in tRNA molecules which can be utilized for priming in vitro reverse transcription reactions (Kohlstaedt, L. A. and T. A. Steitz, *Proc. Natl. Acad. Sci. USA* 89:9652–9656 (1992)), and that even fragments of the recombinant cognate tRNA primer associate with the reverse transcriptase enzyme in vitro and prime cDNA synthesis (Weiss, S. et al. (1992)). However, there appears to be a requirement that the tRNA molecules employed have a 3' sequence which is complementary to the template from which synthesis is directed; even so, the range of tRNA molecules which can act as primers is limited in vitro, and this flexibility may not reflect the tRNA utilization requirements in vivo.

The present method of in vivo cDNA synthesis provides that the in vivo cDNA synthesis primer molecule ("the primer") anneals to a target RNA molecule and that this complex is utilized by the reverse transcriptase enzyme. This aspect of the invention recognizes that it may be desirable, in certain embodiments, to form a duplex between the primer and the reverse transcriptase enzyme, and thereby facilitate the annealing of the primer to the RNA template molecule.

The primer and the reverse transcriptase enzyme may either be present in the cell, or either one or both can be synthesized in or introduced into the cell. Thus, in one embodiment of the present invention, in vivo cDNA synthesis may be performed in a cell line that carries genes encoding a reverse transcriptase enzyme and the primer molecule. The expression of these genes will result in the synthesis of the reverse transcriptase enzyme and the primer in the cell. In other embodiments, the genes encoding the reverse transcriptase and the primer may be expressed under the control of inducible promoters such that the induction of the genes will lead to the expression of the reverse transcriptase and the primer and thereby initiate cDNA synthesis.

More commonly, the primer and the reverse transcriptase enzyme will be introduced into the cell from an external source. A number of techniques have been established for the delivery of biological materials into viable cells. Many of these techniques have been described (*Molecular Cloning; A Laboratory Manual* Cold Spring Harbor Laboratory Press, Cold Spring Harbor, N.Y. (1989); Keown, W. A. et al., *Meth. Enzymol.* 185:527–537 (1990)), and include, but are not limited to, electroporation (Neumann, E. et al., *EMBO J.* 1:841–845 (1982); *Electroporation and electrofusion in cell biology* Neumann, E. et al. eds., Plenum Press, New York (1989); Kamdar, P. et al., *Nucleic Acids Res.* 20:3526 (1992); Rols, M-P. et al., *Eur. J. Biochem.* 206:115–121 (1992); Tsongalis, G. J., et al., *Mutat. Res.* 244:257–263 (1990); Lambert, H., et al., *Biochem. Cell Biol.* 68:729–734 (1990); Yorifuji, T., and H. Mikawa, *Mutat. Res.* 243:121–126 (1990); Winegar, R. A., et al., *Mutat. Res.* 225:49–53 (1989)); DEAE-dextran (Levesque, J. P., et al., *Biotechniques* 11:313–4, 316–8 (1991); Ishikawa, Y., and C. J. Homcy, *Nucleic Acids Res.* 20:4367 (1992)); cationic liposomes (Jarnagin, W. R. et al., *Nucleic Acids Res.* 20:4205–4211 (1992)) or cationic lipids (Walker, C. et al., *Proc. Nat. Acad. Sci. USA* 89:7915–7918 (1992); receptor-mediated delivery (Wagner, E. et al., *Proc. Nat. Acad. Sci. USA* 89:6099–6103 (1992); microinjection (Martin, P. et al., *Dev. Biol.*, 117:574–580 (1986)); protoplast fusion; laser or particle bombardment; and viral vector delivery. One skilled in the art will recognize that each of these techniques has associated advantages and disadvantages and will be able to select the delivery technique most suitable for the cell type being used.

In certain embodiments of the present invention, the technique of delivery of the in vivo cDNA synthesis primer into cells is electroporation. This technique has been used, as described below, to introduce modified tRNA primers, reverse transcriptase enzymes, and modified deoxynucleotide triphosphates into a number of distinct cell types.

When the reverse transcriptase enzyme is introduced into the cell from an external source, the choice of in vivo cDNA synthesis primer will be determined by the type of the reverse transcriptase enzyme selected. There are two commonly used and commercially available types of reverse transcriptase: Avian Myeloblastosis Virus reverse transcriptase and Moloney Murine Leukemia Virus reverse transcriptase. These enzymes are available on a commercial basis from such vendors as: Stratagene, 11011 N. Torrey Pines Road, La Jolla, Calif. 92037; Bethesda Research Laboratories, Inc., P.O. Box 6009, Gaithersberg, Md., 20877; New England Bio Labs, Inc., 32 Tozer Road, Beverly, Mass., 01915; and Boehringer Mannheim Biochemicals, 9115 Hague Road, P.O. Box 50816, Indianapolis, Ind., 46250. The various enzymes have both inherent parameters: fidelity (error rate), processivity (ability to complete cDNA synthesis), and structure (heterodimer vs monomer); and marketing parameters, such as availability and acceptance, which are factors which should be considered in choosing the enzyme.

For the purposes of the present invention, a DNA cassette containing the encoded modified tRNA sequence operatively linked to a promoter sequence was cloned into a bacterial vector. This allowed production of the modified tRNA primer in vitro, using an RNA polymerase which recognized the promoter sequence. The choice of promoter for use in instances where the in vivo cDNA synthesis primer is to be transcribed in vitro will be dictated by the polymerase enzyme to be used in the selected in vitro transcription system. In a preferred embodiment of the present invention, the modified tRNA$^{Pro}$GGG primer was expressed under the control of a bacteriophage T7 promoter in an in vitro transcription system using the T7 RNA polymerase enzyme. The modified tRNA primer produced was isolated and introduced into cells along with the reverse transcriptase enzyme and radiolabeled deoxynucleotide. Following introduction of these exogenous components, the cell was incubated for a sufficient period of time and under suitable conditions to allow in vivo cDNA synthesis to occur. Suitable conditions are generally those under which the cell type in question is usually grown. In preferred embodiments of the present invention, the target cell is incubated for 0.5–2 hours under normal culture conditions for that cell type following introduction of the primer and reverse transcriptase enzyme. As described in the examples listed below, the introduction of a radiolabeled dNTP (for example, [α-$^{32}$P]dCTP) may be used to determine the efficacy of in vivo cDNA synthesis under particular conditions and with particular primers. After incubation of the cells, the cDNA produced in vivo was then extracted from the target cell utilizing the Hirt-extraction protocol (Hirt, B., *J. Mol. Biol.* 26:365–369 (1967)). The extracted cDNA product was found to be double-stranded nucleic acid which was successfully cloned using common cloning procedures. As alternative methodologies, the primer and/or enzyme could be produced from genes introduced into cells; the enzyme could be expressed from a gene within the cell, and the primer introduced into the cell; or the primer could be expressed within the cell and the reverse transcriptase could be introduced from the outside. The inclusion of modified (radiolabeled) deoxynucleotide triphosphates in the reaction was used as a tool to follow the incorporation of deoxynucleotides and is not a requirement of the method; however, it should be noted that inclusion of modified deoxynucleotides provides both a convenient technique of following incorporation and synthesis (when α-labeled deoxynucleotides are used), and provides a means of selecting or distinguishing the products of an in vivo cDNA incorporation reaction (using biotinylated or other deoxynucleotide analogs). Modified deoxynucleotides and deoxynucleotide analogs have been used successfully in all types of polymerase reactions and are obvious techniques to one skilled in the art (Prober, J. M. et al., *Science* 238:336–341 (1987); Klevan, L. and G. Gebeyehu, *Meth. Enzymol.*, 154:561–577 (1987); Chan, V. T-W., et al., *Nucleic Acids Res.* 13:8083–8091 (1985); Lo, Y-M. D., et al., *Nucleic Acids Res.* 16:8719 (1988)).

The products of these reactions can be used in various ways including, but not limited to: the construction of subtractive cDNA libraries; production of specific cytotoxic or light sensitive cDNA products; in vivo DNA sequencing; and cDNA probes for analytical, diagnostic or preparative use.

The following examples serve to illustrate certain preferred embodiments and aspects of the present invention and are not to be construed as limiting the scope thereof.

EXPERIMENTAL

In the experimental disclosure which follows, the following abbreviations apply: eq (equivalents); M (Molar); mM (millimolar); μM (micromolar); N (Normal); mol (moles); mmol (millimoles); μmol (micromoles); nmol (nanomoles); kg (kilograms); gm (grams); mg (milligrams); μg (micrograms); ng (nanograms); L (liters); ml (milliliters); μl (microliters); cm (centimeters); mm (millimeters); μm (micrometers); nm (nanometers); V (volts); μF (microfarads) and ° C. (degrees Centigrade).

In the following Examples, unless otherwise specified, restriction enzymes, T4 DNA ligase, and polynucleotide kinase are obtained from New England Biolabs. The [α-$^{32}$P] dCTP, [α-$^{32}$P]UTP, and [γ-$^{32}$P]ATP are obtained from Amersham Corporation, and Moloney Murine Leukemia Virus reverse transcriptase buffers and enzymes are obtained from Bethesda Research Laboratories. These materials are used according to manufacturer's instructions unless otherwise specified. Electroporation is performed using an electroporator from Invitrogen Corporation, and electroporation cuvettes from BioRad Corporation. Oligonucleotides are obtained from Operon Technologies, Inc, or can be synthesized, e.g., on an Applied Biosystems DNA synthesizer according to the manufacturer's instructions. *Thermus aquaticus* DNA polymerase I is obtained from Perkin-Elmer Cetus. All standard molecular biology techniques are performed according to Sambrook et al. (1989) or Berger and Kimmel (1987), herein incorporated by reference.

Nucleic acid sequences disclosed herein are divided into 10-mer or smaller oligonucleotides as a matter of convenience, and should be interpreted as continuous sequences unless otherwise indicated.

Example 1

I. Synthesis of Genes Encoding tRNA Primers

Figure 2B:
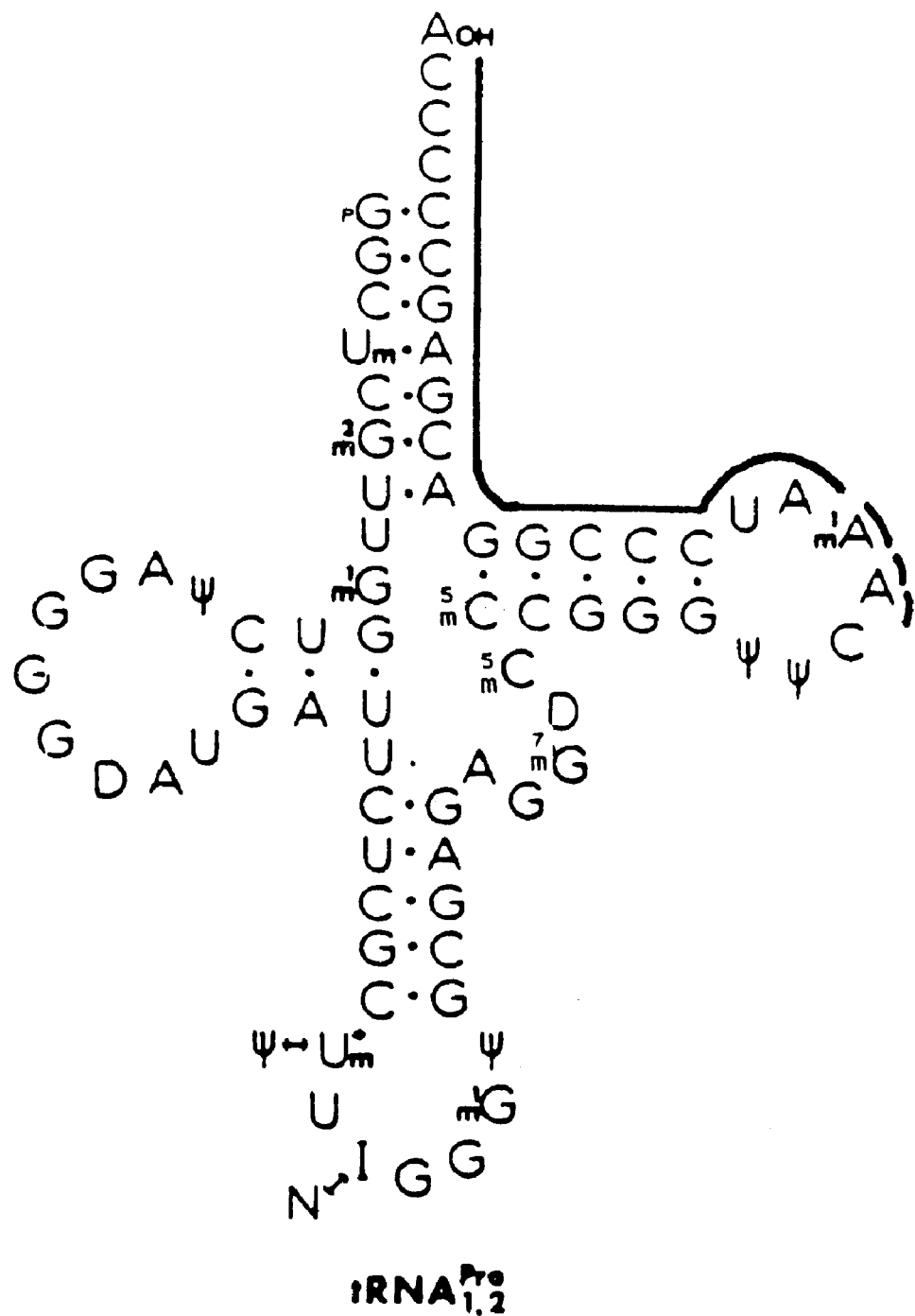
FIG. 2B depicts the structure and sequence of a tRNA molecule corresponding to the "wild type" murine tRNA$_{1,2}$$^{Pro}$ utilized by Moloney murine leukemia virus, in which the solid line defines the 3' nucleotide sequence which anneals to the virion RNA template and primes the retroviral reverse transcriptase reaction.
Figure 3A:
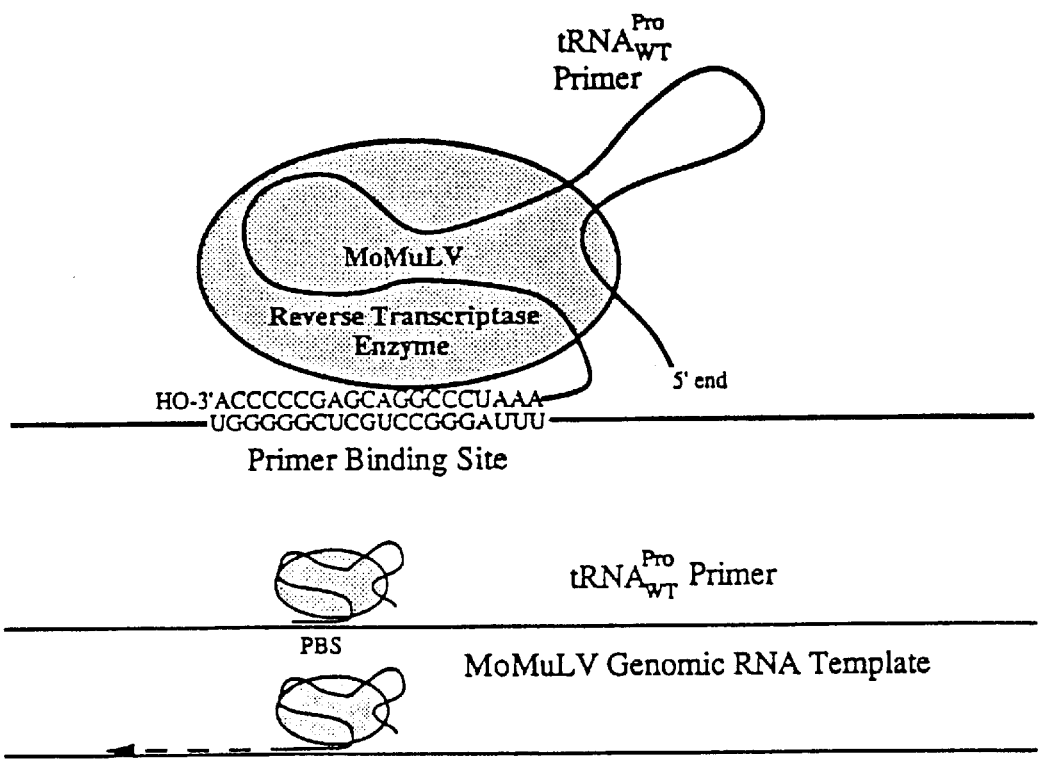
FIG. 3A depicts retroviral cDNA synthesis sequences for both the 3' region of the cognate tRNA$_{wt}$$^{Pro}$ utilized by the Moloney murine leukemia virus, and the complementary Primer Binding Site on the retroviral RNA segment (straight solid line), to which the tRNA binds, and the initial stages of retroviral replication (the dashed line represents cDNA synthesis)

The Moloney Murine Leukemia virus (MoMuLV) utilizes the murine tRNA$_{1,2}$$^{pro}$ isoacceptor molecules as primers for synthesis of retroviral DNA (Harada, F., et al.,*J. Biol. Chem.* 254:10979–10985 (1979); Peters and Dahlberg, *J. Virol.* 31:398 (1979)). These particular tRNA molecules are found complexed with the MoMuLV reverse transcriptase enzyme in the virion, and this complex, in turn, anneals to the primer binding site on the viral RNA genome (see FIGS. 2B and 3A). The MoMuLV reverse transcriptase, capable of utilizing the annealed tRNA molecule as a primer, initiates DNA synthesis, and proceeds to synthesize a DNA molecule that is complementary to the template RNA molecule to which the tRNA primer is annealed.

Figure 2A:
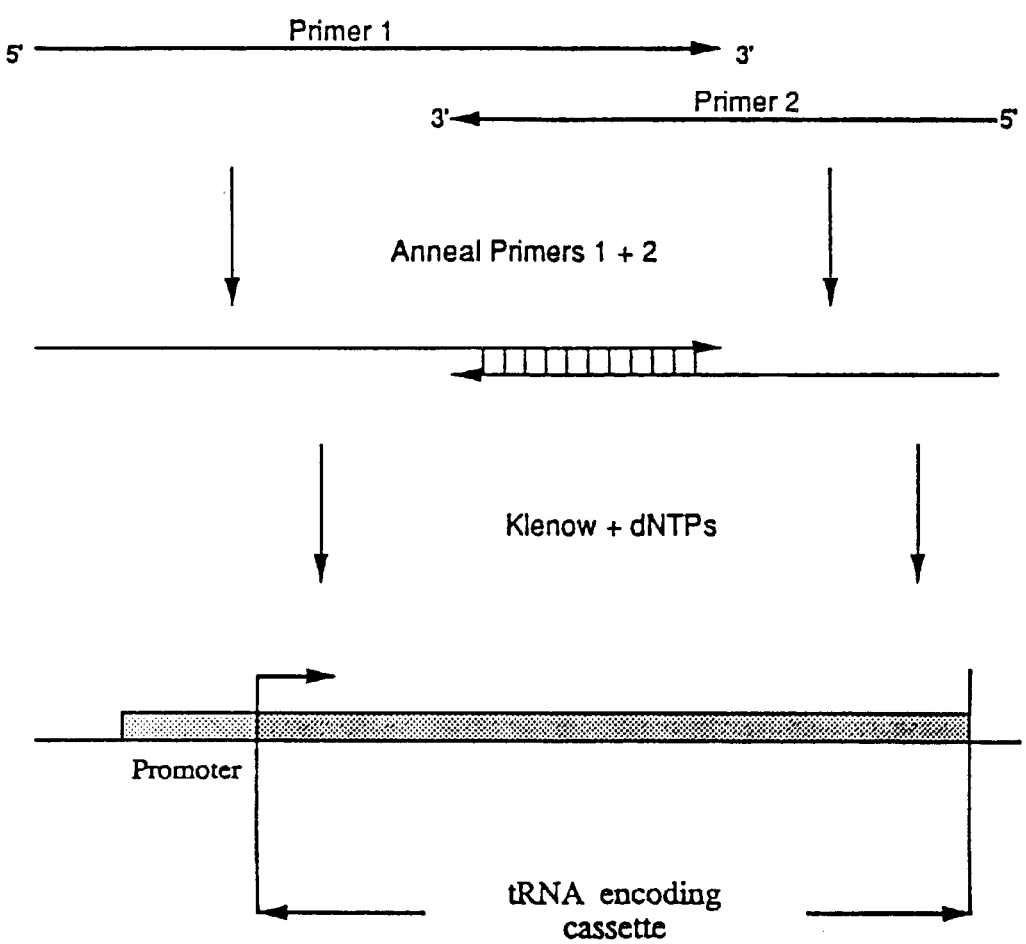
FIG. 2A depicts a schematic diagram of certain techniques involved in cloning of the tRNA$^{Pro}$ gene cassettes.

The nucleotide sequence of murine tRNA$^{Pro}$GGG primer is known (Harada et al., (1979)). Two versions of this tRNA molecule are transcribed in vitro from genetic cassettes which are synthesized using oligonucleotides, then cloned and confirmed by sequence analysis. The deoxyribonucleotide primers used these reactions are depicted below:

Primer No. 1 (SEQ ID No. 1):
5'-ACGGATCCTA ATACGACTCA CTATAGGCTC GTTGGTCTAG GGGTATGATT CTCGCTTGGG GTGCGAG Primer No. 2 (SEQ ID No. 2):
5'-TGGAATTCTC TTCATGGGGG CTCGTCCGGG ATTTGAACCC GGGACCTCTC GCACCCCAAG CGAGAA Primer No. 3 (SEQ ID No. 3):
5'-ACGGATCCTA ATACGACTCA CTATAGAAAA AAATGGTCTA GGGGTATGAT TCTCGCTTGG GGT-GCGAG Primer No. 4 (SEQ ID No. 4):
5'-TGGAATTCTC TTCAAAAAAA AAAAAAAAAA AAAAGAACCC GGGACCTCTC GCACCCCAAG CGAG Primer No. 5 (SEQ ID No. 5):
5'-AAAAAAAAAA AAAAAAAAAA GAACCCGGG
Primer No. 6 (SEQ ID No. 6):
5'-CGAAGCTTTA AAAAAAAAAA AAAAAAAAAG AACCCGGGAC CTCTCGCACC CCAAGCGAG Oligonucleotide primers No. 1 and No. 2 are designed to produce a recombinant tRNA molecule corresponding to the "wild type" murine tRNA$^{pro}$GGG primer as illustrated in FIG. 2A. There are certain differences, in that the in vitro transcribed tRNAs will not contain the modified ribonucleotide bases that exist in their cellular counterparts. However, these modifications have been found to have the same efficacy in terms of both reverse transcriptase-tRNA interaction, and their ability to prime in vitro cDNA synthesis, as the naturally occurring cognate tRNAs (Barat, C. et al. (1989); Weiss, S. et al. (1992); Barat, C. et al. (1991)). The 3' ends of these primers are complementary such that the 3' ends of primer No. 1 and primer No. 2 can be annealed in vitro, then treated with the Klenow fragment of DNA polymerase I in the presence of dNTPs to produce a double-stranded DNA molecule comprising a T7 RNA polymerase promoter-tRNA$_{wt}$ encoding cassette (see FIG. 2A). This primer pair is designed such that this bacteriophage T7 promoter sequence is operatively linked to the 5' end of the tRNA molecule. This promoter-tRNA cassette is flanked with restriction sites to allow the cassette to be cleaved from a cloning vector, and an EarI restriction site is incorporated into the 3' end of the cassette so that digestion of the cassette with the EarI endonuclease prior to in vitro transcription reactions results in linearization of the template (hence termination of transcription) at the exact 3' end of the encoded tRNA sequence. The nucleotide sequences of primer Nos. 1 and 2 are set forth in SEQ I.D. Nos. 1 and 2, respectively.

Figure 3B:
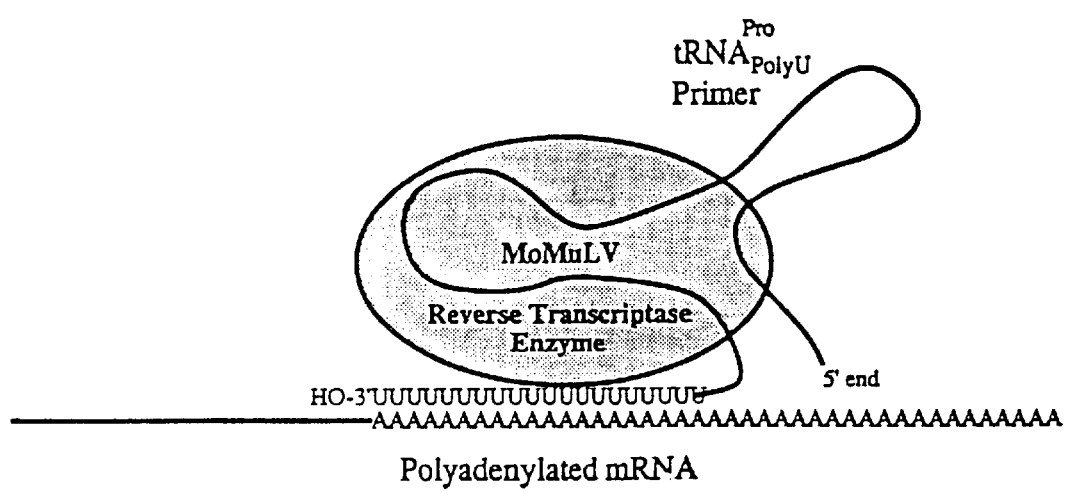
FIG. 3B depicts in vivo cDNA synthesis from a polyadenylated messenger RNA, in which sequences are shown for both the 3' region of the tRNA$_{PolyU}$$^{Pro}$ which has been modified and synthesized in vitro, and the mRNA polyadenylated 3' segment to which the tRNA binds, as well as the initial stages of in vivo cDNA synthesis (the dashed line)
Figure 3B:
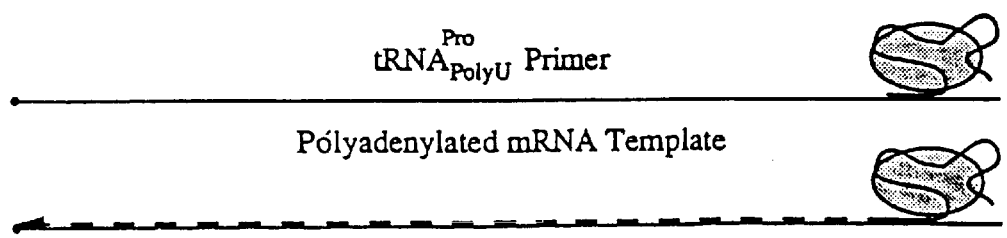

A second primer pair (primer Nos. 3 and 4) is designed to encode a modified form of the tRNA molecule, the modified tRNA molecule being termed tRNA$_{PolyU}$, as follows:
SEQ. ID No. 7
5'-GAAAAAAAUG GUCUAGGGGU AUGAUUCUCG CUUGGGGUGC GAGAGGUCCC GGGUUCUUUU UUUUUUUUUU UUUUUU As with the tRNA$_{wt}$, a bacteriophage T7 promoter sequence is operatively linked to the 5' end of the tRNA sequence and flanking restriction sites and an EarI site is incorporated. Primer No. 4, encompassing the 3' end of the tRNA$_{PolyU}$ molecule, encodes a poly(U) sequence in place of the 3' terminal nucleotides of the wild type tRNA molecule (compare the tRNA sequences in FIGS. 3A and 3B). Primer Nos. 3 and 4 are set forth in SEQ I.D. Nos. 3 and 4 respectively.

Equal molar ratios of primer Nos. 1 & 2, and 3 & 4 are kinased using T4 DNA kinase (polynucleotide kinase). The kinased oligomer primer pairs Nos. 1 and 2, and primer Nos. 3 and 4 are annealed (80° C. for 3 minutes, slowly cooled from 60° C. to 37° C. over 20 minutes) in Klenow buffer (50 mM Tris-chloride (pH 7.6) at 25° C., 10 mM MgCl$_2$, 10 mM β-mercaptoethanol), containing 2 mM dNTPs. The annealed primer pairs are then incubated for 30 minutes at 37° C. with 10 units of the Klenow fragment of DNA polymerase I in a 30 μl volume to complete double-stranded DNA synthesis. These double-stranded DNA cassettes are then extracted and precipitated using commonly available techniques, resuspended in 1/10 TE buffer (1 mM Tris-chloride, 0.1 mM EDTA (pH 8.0)), and ligated into the dephosphorylated SmaI site in the pUC18 cloning vector (Yannish-Perron et al., Gene 33:103–119 (1985)). The wild type tRNA gene, created by the combination of primer Nos. 1 and 2, is cloned into pUC18 to create pUC18-T7tRNA$_{wt}$. The modified tRNA gene, created by a combination of primer Nos. 3 and 4, is cloned into pUC18 to create pUC18-T7tRNA$_{PolyU}$. The sequences and orientations of these two promoter-tRNA cassettes are verified by DNA sequencing, which is performed using Sequenase™ 2.0 (U.S. Biochemicals) in accordance with the supplier's recommendations.

II. Synthesis of tRNA Primers

Cloned DNA molecules encoding either tRNA$_{wt}$ or tRNA$_{PolyU}$ are produced as described above. Transfer RNA molecules are produced from these cloned tRNA genes by incubating the tRNA gene in the presence of bacteriophage T7 RNA polymerase. RNA polymerases generally proceed to synthesize an RNA molecule that is complementary to the template DNA until they encounter a transcription termination signal in the template DNA sequence, or simply run off the DNA template. To ensure that the tRNA molecule produced by the action of the T7 RNA polymerase is properly terminated at the end of the tRNA gene, the tRNA template provided is linearized at the end of the tRNA gene. This can be achieved in a number of ways.

One technique involves cutting the cloned insert by restriction enzyme digestion. Digestion with EarI restriction endonuclease removes the promoter-tRNA cassette from pUC18-T7tRNA$_{wt}$, digesting in vector sequences substantially 5' to the T7 promoter sequence, and digesting precisely at the 3' end of the tRNA gene template.

Because the EarI restriction site at the 3' end of the tRNA$_{PolyU}$ insert is found to be resistant to digestion, the above approach may not be used with the pUC18-T$^7$tRNA$_{PolyU}$ cloning vector. To circumvent this problem an alternative technique, utilizing the polymerase chain reaction (PCR), is used both to amplify the specific promoter-tRNA$_{PolyU}$ fragment, and define the end of the tRNA$_{PolyU}$ coding template. For this purpose, two oligonucleotide primers are used: the first primer is a commercially available primer which anneals to sequences in the pUC18 vector located 5' to the inserted T7 promoter region with the 3' end directed towards the T7 promoter region sequence, and the second is a "Reverse tRNA Primer" (set forth in SEQ I.D. No. 5) which anneals to bases of the desired T7 promoter-tRNA$_{PolyU}$ cassette, such that the 5'-most base of the Reverse tRNA Primer is the last 3' base of the encoded tRNA$_{PolyU}$ template, as follows:
SEQ. ID No. 8
5'-GAAAAAAATG GTCTAGGGGT ATGATTCTCG CTTGGGGTGC GAGAGGTCCC GGGTTCTTTT TTTTTTTTT TTTTTT The PCR is performed according to the following conditions: PCR buffer: 67 mM Tris (pH 9.2 at 25° C., 16.6 mM (NH$_4$)$_2$SO$_4$, 1.5 mM MgCl$_2$; 50 ng of each primer, approximately ×10$^8$ molecules of the pUC18-tRNA$_{PolyU}$ construct, and 250 μM concentrations of each of the deoxynucleotide triphosphates. The reaction mixtures are heated to 100° C. for 3 minutes, then cooled to 15° C. The tubes are centrifuged briefly to collect the contents, then 1 unit of Taq polymerase and a drop of mineral oil are added to each 20 μl reaction. The reaction is performed in 40 cycles with the following regimen: 1 minute at 94° C.; then 1 minute at 55° C. The amplified products are pooled from 5 reactions, rendered blunt-ended with Klenow fragment and 1 mM dNTPs, extracted to remove protein and traces of mineral oil, and EtOH precipitated using standard protocols. The pellet is rinsed with 70% ethanol (EtOH) and dried. The pellet is then resuspended in 1/10 TE, and fragments are examined on a 2% agarose/TAE gel against known size standards.

It should be noted that the PCR is known to allow incorporation of single nucleotides (usually deoxyriboadenylic acid residues) to the ends of the amplified product in a template-independent manner (Clark, J. M., *Nucleic Acids Res.* 16:9677–9686 (1988)). However, this template-independent incorporation occurs rarely, and when an extra adenine residue is added, it is added to the 3' end, which is upstream of the T7 promoter, not to the template-encoding sequence. Radiolabeled products of subsequent in vitro transcription reactions utilizing these templates are examined using denaturing polyacrylamide electrophoresis with known size standards, and are of the desired size.

Linear DNA fragments containing the T7 promoter-$tRNA_{wt}$ cassette and the T7 promoter-$tRNA_{PoLyU}$ cassette are used as the template molecules for the in vitro production of the tRNA molecules. This is achieved by run-off transcription using the bacteriophage T7 RNA polymerase enzyme (see below).

For in vitro production of $tRNA_{wt}$, reactions are performed using EarI-linearized pUC18-$tRNA_{wt}$template. For in vitro production of $tRNA_{PoLyU}$, the PCR-amplified T7-$tRNA_{PoLyU}$ cassette is used as the template; alternatively, a DraI sensitive T7-tRNAP$_{PoLyU}$ cassette is linearized and used as template for the in vitro transcription reactions (produced with oligomers Nos. 3 and 6, using the same protocols used for the production of the EarI compatible T7-$tRNA_{PoLyU}$ template). For the in vitro reactions the following conditions may be utilized (Gurevich, V. V. et al., *Anal. Biochem.* 195:207–213 (1991): Briefly, to RNase-free eppendorf tubes the following components are added at 25° C.: 80 mM Hepes-KOH (pH 7.5), 12 mM $MgCl_2$, 20 mM DTT, 5 mM dNTPs, 2 mM spermidine; RNase-free $dH_2O$; 50–100 µg/ml template DNA and 5 µl of [$\alpha$-$^{32}$P]ATP (30 mCi; 3000 Ci/mmol; added in order to examine and quantify the products). The reaction components are mixed, and the reaction is then initiated with the addition of T7 RNA polymerase enzyme reaction mix (to a final concentration of 1200–1800 U/ml). The tubes are then incubated at 37° C. for 4 hours. RNase-free DNase is then added to the reactions, and the digestion of template DNA allowed to proceed for 15–30 minutes; at this point, small aliquots of the reaction mixture can be removed in order to determine the efficiency of incorporation. This determination can be achieved by cold trichloroacetic acid precipitation of an aliquot of the reaction mixture in the presence of an excess of RNase-free carrier DNA. The control for this determination, total counts, is performed on unprecipitated material from the same reaction mixture. To each of the reaction mixtures is then added 150 µl of RNase-free $dH_2O$ and 20 µl of 3M NaOAc and the mixtures are extracted with an equal volume of phenol/$CHCl_3$ (pH 6.5) (phenol buffered at pH 6.5 is used to minimize the possibility of base-catalyzed hydrolysis of the RNA product), followed by $CHCl_3$. The products are precipitated with 2-propanol, the pellets rinsed, and the precipitate dried. The primer product is resuspended in RNase-free $dH_2O$, and an aliquot checked for size using autoradiographic exposure of a polyacrylamide/urea gel run with known size standards.

III. Chemical Synthesis Using Solid Phase Support

The ability to chemically synthesize unmodified oligonucleotides and 2'-O-methyloligoribonucleotides in high yields on solid phase permits the present invention to be readily adapted for use in preparative, analytical and therapeutical applications. Synthetic techniques and reagents useful for modified oligoribonucleotide production (e.g. Sprout, B. S. et al., *Nucleic Acids Res.* 17:3373–3386 (1989), incorporated herein by reference), provide a number of embodiments which could not be achieved if the RNA primers are produced in vitro from a DNA template. For example, 2'-O-methyloligoribonucleotides are known to be resistant to RNase activity (Sprout, B. S. et al., (1989); Inoue, H. et al., *FEBS Lett.* 215:327–330 (1987)). Therefore, the use of these modified RNA molecules as primers for an in vivo cDNA synthesis reaction, in place of oligoribonucleotides, results in a resistance to RNase H-catalyzed removal of the initial cDNA synthesis primer (including any existing modifications). These primers can then be biotinylated, $^{32}$P-labeled, or contain sequence elements such as restriction sites which will be copied and incorporated during second-strand cDNA synthesis following base-catalyzed hydrolysis of the original template (the 2'-O-Methyl primer will protect the annealed complementary portion of the original RNA template as well). These modifications do not appear to disrupt the ability of the primers to associate with proteins (Sprout, B. S. et al., (1989)), and the modified oligoribonucleotides anneal with the expected specificity. The elimination of the 2'-OH group renders an RNA primer more resistant to base-catalyzed (nucleophilic) attack on the neighboring 3', 5'-phosphodiester bond, and it is resistant to a variety of ubiquitous RNases.

IV. Experimental Design

The modified tRNA primer synthesized as described above is used for in vivo cDNA synthesis reactions in numerous different cell lines. Control reactions are also performed in the absence of primer, with an oligo(dT) primer, or with the in vitro-transcribed wild-type $tRNA_{wt}$ molecule as primer. In these experiments, the primer is introduced into cells via electroporation, along with Moloney Murine Leukemia Virus reverse transcriptase and [$\alpha$-$^{32}$P]dCTP. The radiolabeled dCTP is included to facilitate the analysis of the products of these reactions. Care in the preparation of the target cells for the in vivo cDNA synthesis reaction is important, and an assessment of the mode of primer-reverse transcriptase (and, perhaps modified deoxynucleotide triphosphate, or analog) delivery should be carefully considered. Many alternatives exist, as will be obvious to one skilled in the art; some of these techniques are mentioned above, and use of electroporation in the following Examples should not be construed as limiting the scope of the invention.

Following electroporation of the reaction components into target cells and incubation of the cells, the products of the reaction are extracted from the cells by the Hirt extraction technique (Hirt, B., *J. Mol. Biol.* 26:365–369 (1967)), and digested to completion with ribonuclease A. Following phenol/chloroform extraction and ethanol precipitation the product is assessed by quantifying incorporation, and by examining of the size of the products separated on agarose gels, with known size standards, using autoradiography. Further, S1 nuclease treatment, and RNase H treatment are used to determine the nature of the DNA product.

V. In Vivo cDNA Synthesis in Insect Cells

The insect Sf9 cell line is obtained from the American Type Culture Collection (ATCC), and maintained as recommended by the supplier. For in vivo cDNA synthesis, the cells are suspended at a concentration of $1\times10^7$ cells/ml in Grace's medium.

Prior to electroporation, the reaction components comprising the reverse transcriptase enzyme (1000 units), the tRNA primer (5 µg) and [$\alpha$-$^{32}$P]dCTP (50 µCi) are mixed in a total volume of 50 µl in reverse transcription buffer (obtained from BRL) containing dithiothreitol (DTT) (10 mM), and incubated at room temperature for 10 minutes.

The Sf9 cells ($5\times10^6$ cells in 0.5 ml) are then added to the reaction components and the mixture is transferred into a chilled 0.4 cm electroporation cuvette. Electroporation is then performed with the electroporator set at 200V, 250 $\mu$F and infinite resistance.

Following electroporation, 1 ml of warmed Grace's medium is added to the cuvette and the mixture is transferred to a plastic tube (Falcon #2059). The mixture is then incubated for one hour at 37° C. Although the normal temperature for maintaining the Sf9 insect cell line is approximately 25° C., the obtainment of improved enzyme activity is the primary concern.

Following the incubation period at 37° C., the cells are pelleted by centrifugation for 5 minutes at setting 5 in an Eppendorf Model 5415C microfuge (or equivalent). The radioactive supernatant is carefully removed and disposed of properly, and 1 ml of 0.6% sodium dodecyl sulfate (SDS), 10 mM EDTA (pH 7.5) is added to the cell pellet. Immediately this pellet is gently resuspended with a large bore Pipetman P1000 tip (a portion of the tip removed to increase the bore diameter, thus decreasing the shear forces and fragmentation of genomic DNA). The viscous lysate is placed on ice for 5 minutes, then 250 $\mu$l of 5M NaCl is added and the tube inverted several times to mix. The tubes are then placed on ice. Following the incubation period of this Hirt extraction (2–12 hours), the extract is centrifuged for 20 minutes at top speed in a cold Eppendorf microfuge. The supernatant is carefully withdrawn from the pellet (which is discarded in radioactive waste), and the supernatant split between two new 1.5 ml microfuge tubes. These supernatants are extracted twice with phenol/chloroform (1:1), then once with chloroform. The nucleic acid fraction is then precipitated with the addition of 1/10 volume of 3M NaOAc and 1/6 volume of 2-propanol; the pellets are rinsed with 70% ethanol, and then dried. The pellets are resuspended in 18 $\mu$l of 1 mM Tris-chloride, 0.1 mM EDTA (pH 7.0); the resuspended nucleic acid fraction is treated with ribonuclease A (2 $\mu$l of 10 mg/ml stock solution), at 37° C. for 15 minutes, followed by the addition of 30 $\mu$l of 1 mM Tris-chloride, 0.1 mM EDTA (pH 7.0). The solution is then extracted once with phenol/chloroform (1:1), then once with chloroform. The nucleic acid fraction is then precipitated with the addition of 1/10 volume of 3M NaOAc and two volumes of ethanol; the pellets are rinsed with 70% ethanol, and dried. Cerenkov counts are obtained on the dried pellets, and the pellets are resuspended and aliquots counted with scintillant. The products are electrophoresed on agarose/TAE gels with radiolabeled molecular weight standards. The gels are then stained with ethidium bromide, dried and examined by autoradiography.

VI. In Vivo cDNA Synthesis in Hamster Cells

The hamster CHO cell line is obtained from the ATCC, and is maintained as recommended by the ATCC. Prior to electroporation, the CHO cells are removed from monolayer culture using a trypsin/EDTA solution. The detached cells are counted, rinsed in PBS and resuspended in PBS at $1\times10^7$ or $1\times10^8$ cells/ml. The reaction components are the reverse transcriptase enzyme (1000 units), the tRNA primer (5 $\mu$g), and [$\alpha$-$^{32}$P]dCTP (50 $\mu$Ci), mixed in a total volume of 50 $\mu$l in reverse transcription buffer (BRL) containing DTT (10 mM), and incubated at room temperature for 10 minutes. Following preincubation, 0.5 ml of the CHO cells are added to the mixture, the cells mixed and immediately transferred to the chilled 0.4 cm electroporation cuvette. Electroporation is performed under the following conditions: 330V, 1000 $\mu$F and infinite resistance. After electroporation, 1 ml of warmed, $CO_2$-equilibrated Ham's medium (GIBCO) is added to the cuvette, the mixture is transferred to a plastic tube (Falcon #2059), and the mixture is then incubated for one hour at 37° C.

Following the incubation period, the cells are pelleted by centrifugation for 5 minutes at setting 5 in an Eppendorf Model 5415C microfuge (or the equivalent). The radioactive supernatant is carefully removed and disposed of properly, and 1 ml of 0.6% SDS (sodium dodecyl sulfate), 10 mM EDTA (pH 7.5) is added to the cell pellet. Immediately this pellet is gently resuspended with an increased bore Pipetman P1000 tip. The viscous lysate is placed on ice for 5 minutes, then 250 $\mu$l of 5M NaCl is added and the tube inverted several times to mix. The tubes are then placed on ice. Following the incubation period of this Hirt extraction (2–12 hours), the extract is centrifuged for 20 minutes at top speed in a cold eppendorf microfuge. The supernatant is carefully withdrawn from the pellet (which is discarded in radioactive waste), and the supernatant split between two new 1.5 ml microfuge tubes. These supernatants are extracted twice with phenol/chloroform (1:1), then once with chloroform. The nucleic acid fraction is then precipitated with the addition of 1/10 volume of 3M NaOAc and 1/6 volume of 2-propanol; the pellets rinsed with 70% ethanol, and dried. The pellets are resuspended in 18 $\mu$l of 1 mM Tris-chloride, 0.1 mM EDTA (pH 7.0); the resuspended nucleic acid fraction is treated with ribonuclease A (2 $\mu$l of 10 $\mu$g/ml stock solution), at 37° C. for 15 minutes, followed by the addition of 30 $\mu$l of 1 mM Tris-chloride, 0.1 mM EDTA (pH 7.0). The solution is then extracted once with phenol/chloroform (1:1), then once with chloroform. The nucleic acid fraction is then precipitated with the addition of 1/10 volume of 3M NaOAc and two volumes of ethanol; the pellets rinsed with 70% ethanol, and dried. Cerenkov counts are then obtained on the dried pellets as described in section V.

VII. In Vivo cDNA Synthesis in Human Cells

The human HeLa cell line is obtained from the ATCC, and is maintained as recommended by the ATCC. Prior to electroporation, the HeLa cells are removed from monolayer culture using a trypsin/EDTA solution. The detached cells are counted, rinsed in PBS and resuspended in PBS at $1\times10^7$ cells/ml. The reaction components are the reverse transcriptase enzyme (1000 units), the tRNA primer (5 $\mu$g), and [$\alpha$-$^{32}$P]dCTP (50 $\mu$Ci), mixed in a total volume of 50 $\mu$l in reverse transcription buffer (BRL) containing DTT (10 mM), and incubated at room temperature for 10 minutes. Then 0.5 ml of HeLa cells ($5\times10^6$) are added to the reaction components and the mixture is transferred into a chilled 0.4 cm electroporation cuvette (BioRad). Electroporation is then performed at the following settings: 330V, 1000 $\mu$F and infinite resistance. After electroporation, 1 ml of warmed, $CO_2$-equilibrated Eagle's minimal essential media (GIBCO) is added to the cuvette, the mixture is transferred to a plastic tube (Falcon #2059), and the mixture is then incubated for one hour at 37° C.

Following the incubation period, the cells are subjected to the Hirt extraction as described in section V, and Cerenkov counts are obtained on the dried pellets.

The following conditions are used as controls for the in vivo cDNA synthesis reactions in all of the cell lines tested: All reactions contain 50 $\mu$Ci of [$\alpha$-$^{32}$P]dCTP (approximately 3000 Ci/mmol). When included, 1000 units of reverse transcriptase (MoMuLV; BRL) are added to the reaction mixture. In reactions requiring tRNA primer, 1–10 $\mu$g of primer is added per 0.5 ml of cells, with the amount determined by the desire to form complexes with all available reverse transcriptase enzyme. The oligo(dT) primer is desirably composed of oligomers of 12–18 bases of deoxyribothymidylic acid; 1 or 5 µg of this oligonucleotide primer is added to reactions where indicated.

VIII. Analysis of Products

Figure 5:
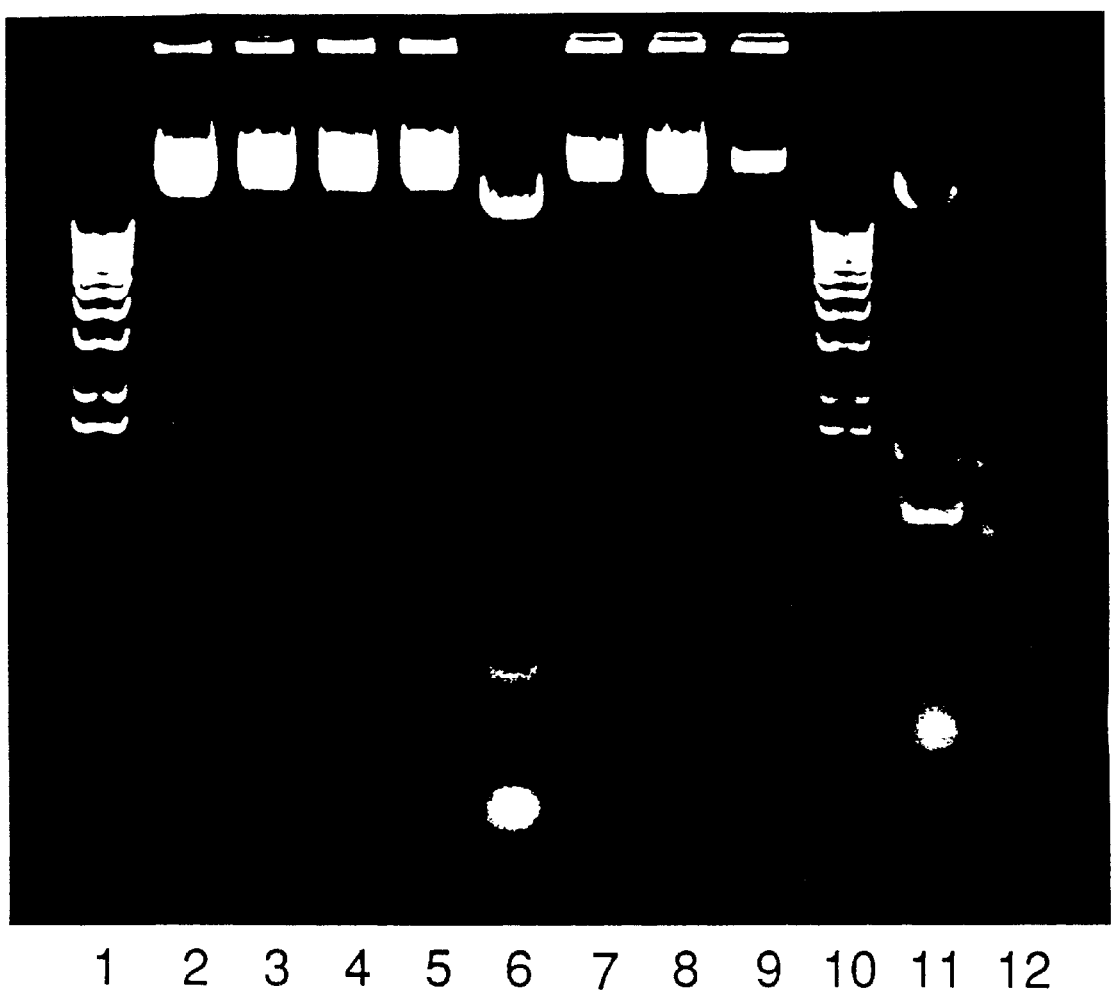
FIG. 5 is a photographic reproduction of an ethidium bromide-stained 1% agarose/TAE gel of in vivo cDNA products from insect Sf9 cells, in which lanes 1 and 10 represent a 1 kb ladder (BRL), lanes 2 and 6 represent control ([α-$^{32}$P]dCTP alone), lanes 3 and 7 represent control ([α-$^{32}$P]dCTP+reverse transcriptase), lanes 4 and 8 represent control ([α-$^{32}$P]dCTP+reverse transcriptase+tRNA$_{wt}$), lanes 5, 9, 11 and 12 represent experimental with modified tRNA primer ([α-$^{32}$P]dCTP+reverse transcriptase+tRNA$_{PolyU}$). In this example, the samples in lanes 11 and 12 are not treated with RNase A, the samples in lanes 2–5, and 11 are electroporations in 0.4 cm cuvettes, and the samples in lanes 6–9, and 12 are electroporations in 0.2 cm cuvettes.
Figure 6:
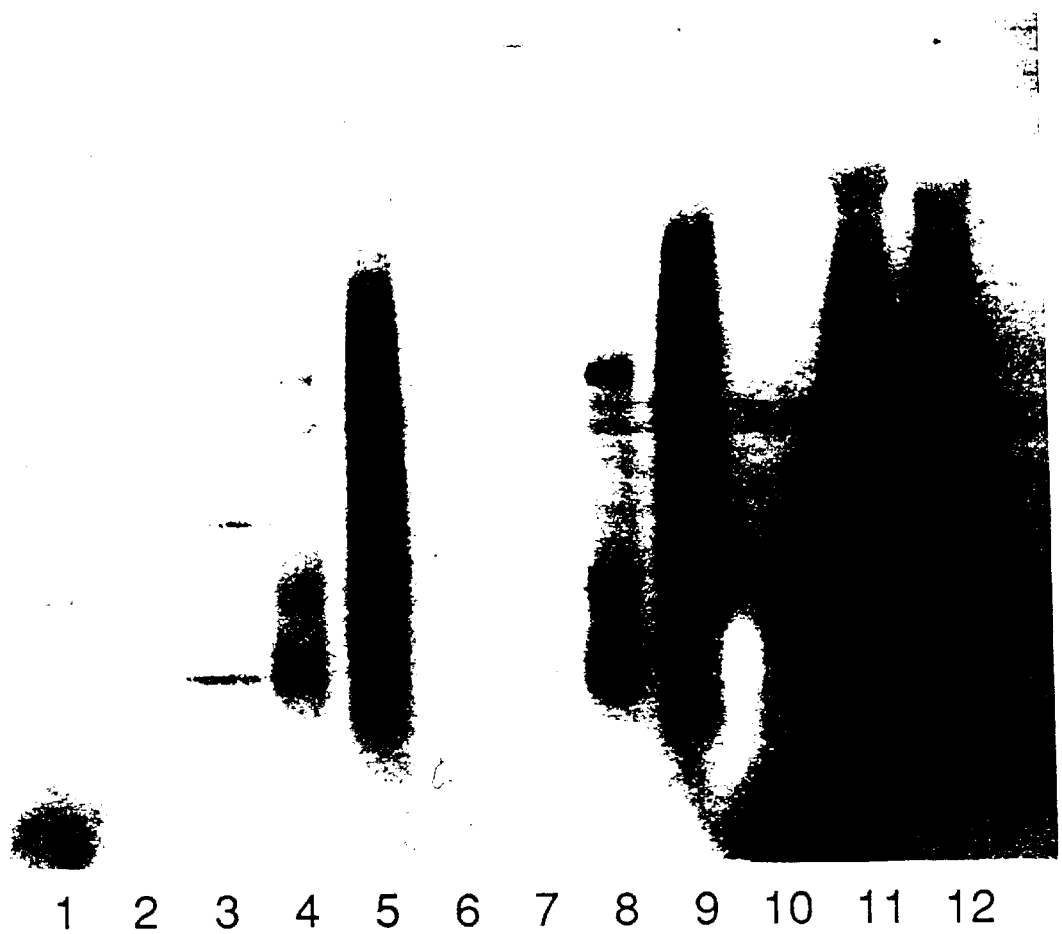
FIG. 6 is a photographic reproduction of an autoradiograph of the gel image depicted in FIG. 5.
Figure 7:
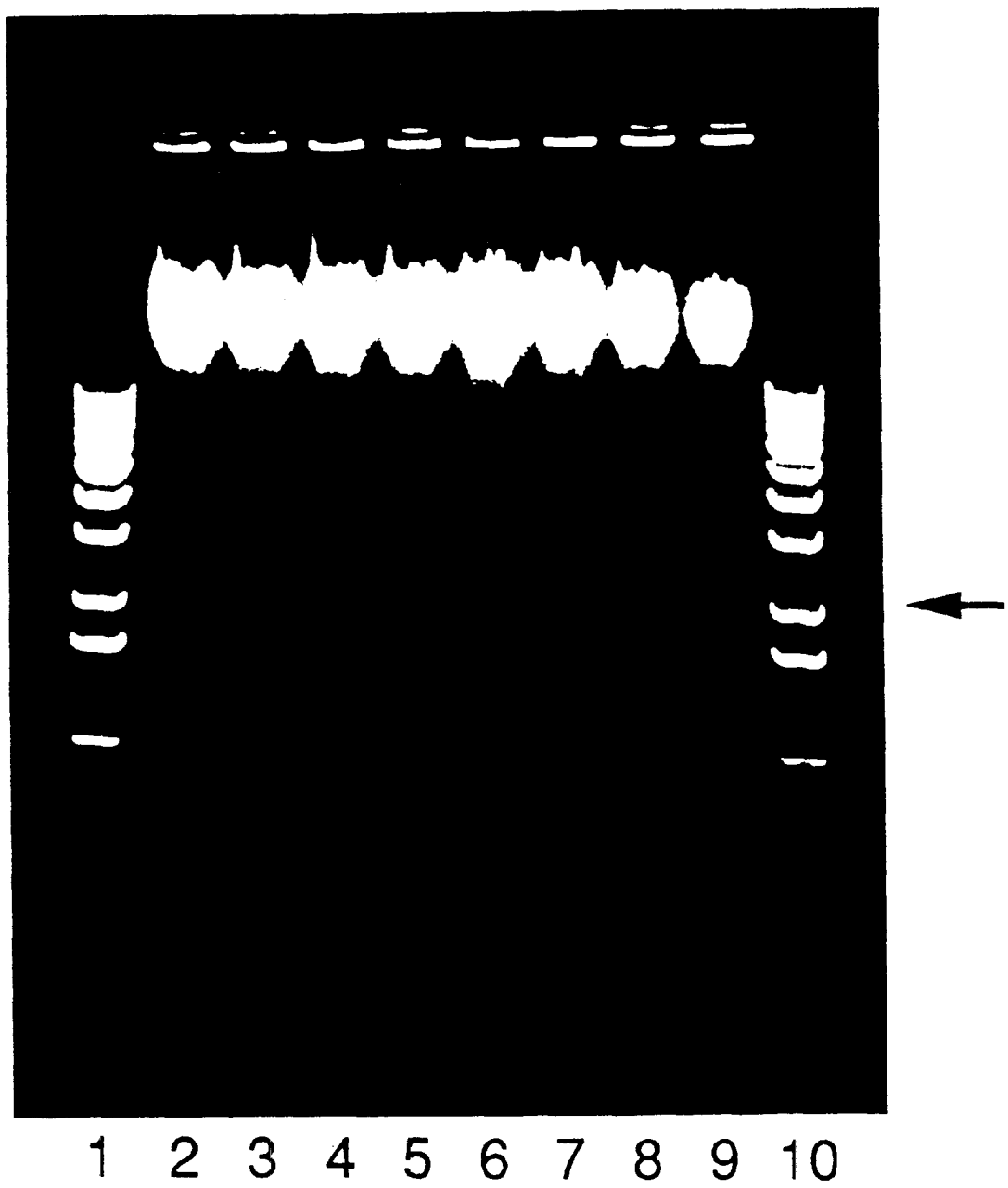
FIG. 7 is a photographic reproduction of an ethidium bromide stained 1% agarose/TAE gel of in vivo cDNA products from Hamster (CHO) cells, in which lanes 1 and 10 represent a 1 kb ladder (BRL), lanes 2 and 6 represent control ([α-$^{32}$P]dCTP alone), lanes 3 and 7 represent control ([α-$^{32}$P]dCTP+reverse transcriptase), lanes 4 and 8 represent control ([α-$^{32}$P]dCTP+reverse transcriptase+tRNA$_{wt}$), lanes 5 and 9 represent experimental with modified tRNA primer ([α-$^{32}$P]dCTP+reverse transcriptase+tRNA$_{PolyU}$)

As noted in sections V, VI and VII, Cerenkov counts can be obtained on the dried pellets; the pellets can be resuspended (and aliquots counted with scintillant), and the products electrophoresed on agarose/TAE gels. These gels are run with radiolabeled molecular weight standards, and the gels can be stained with EtBr (see FIGS. 5, 7, and 9) and dried and examined by autoradiography (see FIGS. 6, 8, and 10).

Figure 10:
FIG. 10 is a photographic reproduction of an autoradiograph of the gel image depicted in FIG. 9.

The reaction products are treated with S1 nuclease to examine the nature of the polydeoxyribonucleotide product (s). Although S1 nuclease will digest a double-stranded nucleic acid molecules to a limited extent, the enzyme works most efficiently on single-stranded nucleic acid substrates; thus polynucleotides which are single-stranded (or contain single-stranded regions) are digested to completion very quickly by S1 nuclease treatment (Sambrook 1989). As is seen in FIG. 10, samples treated with S1 nuclease, when compared with untreated samples, show no appreciable degradation (FIG. 10: compare lanes 2 & 3, and lanes 4 & 5). Indeed, the prominent cDNA product (approximately 1.9 kb in size), which appears in the in vivo cDNA synthesis reaction obtained with the $tRNA_{wt}$ primer, shows no appreciable difference before and after S1 nuclease treatment (FIG. 10: compare lanes 2 & 3).

To further identify the in vivo cDNA product(s), the S1 nuclease treatment is performed on parallel samples before and after ribonuclease H treatment. Ribonuclease H has the activity of digesting the RNA strand of a DNA-RNA heteroduplex. If the double-stranded cDNA product is a heteroduplex, then treatment of the material with ribonuclease H followed by treatment with S1 nuclease will result in degradation of the material and loss of an autoradiographic signal in the higher molecular weight range of an agarose/TAE electrophoretic gel. When these experiments are done, the reaction products appear indistinguishable from the products of S1 nuclease treatment alone. However, the experiments performed with RNase H and S1 nuclease treatment will be repeated in order to rule out heteroduplex in vivo cDNA product.

IX. Cloning in Vivo Synthesized cDNA Products

The double-stranded cDNA products from the reactions, above are cloned into vectors using accepted cloning techniques. Briefly, cells are electroporated with the modified tRNA primer, reverse transcriptase enzyme, and [$\alpha$-$^{32}$P] dCTP (to follow incorporation). Following electroporation and incorporation, the cells are treated as described in Sections V, VI and VII above. The final pellets are rinsed with 70% ethanol, and dried. Cerenkov counts are obtained on the dried pellets, and the pellets are resuspended and aliquots are counted with scintillant. The products are electrophoresed on agarose/TAE gels with radiolabeled molecular weight standards. The gels are stained with EtBr (see FIGS. 5, 7, and 9), dried and examined by autoradiography (see FIGS. 6, 8, and 10).

It is probable that any second strand cDNA synthesis which occurs with this in vivo cDNA synthesis reaction is primed by the 3' end of the first strand cDNA product. RNase H activity acts through RNA template degradation to free the 3' end of the first strand cDNA product and allow flanking sequences to become accessible to annealing by this 3' end. This is a mechanism common in in vitro cDNA synthesis with this enzyme (Okayama, H., et al. *Recombinant DNA Methodology*, Academic Press, Inc., pages 235–260 (1989)).

To insure that the ends of the cDNA products are accessible for cloning, the in vivo cDNA reaction products are treated with S1 nuclease and rendered blunt-ended with T4 DNA polymerase and high concentrations of dNTPs, prior to the addition of adapters or linker molecules. It is important that S1 nuclease be diluted immediately before use, and that the concentration used is determined with small portions of the cDNA product prior to scale-up reactions. Following RNase A treatment, extraction and precipitation, the cDNA is resuspended in S1 nuclease buffer: 200 mM NaCl, 50 mM NaOAc (pH 4.5), 1 mM $ZnSO_4$, 0.5% glycerol and treated with approximately 100 units of diluted S1 nuclease per µg of cDNA for 30 minutes at 37° C. (Kimmel, A. R., and S. L. Berger, *Guide to Molecular Cloning Techniques*, Academic Press, pages 328–329 (1987)). EDTA is added to 20 mM to stop the reaction. The products are extracted twice with buffered phenol/chloroform, then once with chloroform. To the tube containing the aqueous phase are added 1/10 volume of sodium acetate and two volumes of ethanol, and the reaction mixture is placed at −70° C. for 30 minutes. The tube is centrifuged for 15 minutes in a cold microfuge, and the supernatant is discarded. The pellet is carefully rinsed with 80% ethanol and dried in a speedvac (Savant).

The product is treated with T4 DNA polymerase in the presence of high levels of dNTPs to insure that the ends are blunted. The cDNA product is suspended in T4 DNA polymerase buffer (50 mM Tris-HCl (pH 8.3), 50 mM NaCl, 10 mM $MgCl_2$, 10 mM DTT). A stock solution containing each of the deoxynucleotide triphosphates is added to achieve a 500 µM final concentration. Ten units of T4 DNA polymerase is then added to a final volume of 50 µl, and the reaction is incubated at 37° C. for 30 minutes. The reaction is stopped with the addition of EDTA to 20 mM. Once again, the products are extracted, precipitated, and the pellet rinsed and dried, as described in section V.

Adapters or linkers can now be added to the cDNA product. The use of annealed hemiphosphorylated adapters (Promega; only the 5' blunted end of the adapter is phosphorylated) is considered advantageous in that it allows cloning of the cDNA product after ligation of the adapters and elimination of the excess unligated adapters, without digestion of the cDNA insert to remove linker concatemers. In addition, the step of removing the excess adapters, necessary to eliminate "linker library" construction, can be utilized as well for sizing the cDNA prior to ligation into a vector.

Alternatively, annealed unphosphorylated linkers (Boehringer Mannheim) can be utilized and the excess unligated linkers can be removed simply by heating the ligation product briefly in the range of 60° C. to 70° C. This melts the unligated sticky ends, and the ligated, linkered cDNA product can be separated away by column chromatography or gel electrophoresis.

The concentrations of molar equivalent of ends of cDNA and adapters are calculated, and an approximate 20 fold excess of adapters or linkers is used in the ligation reaction (Wu, R. et al., *Meth. Enzymol.* 152:343–349 (1987)). The ligation reaction is performed as follows: to a tube is added 2 µl of 10×ligation buffer (666 mM Tris-HCl (pH 7.6), 100 mM $MgCl_2$, 100 mM DTT, 3 mM ATP, 10 mM spermidine-HCl, 10 mM hexaminecobalt chloride, 2 mg/ml bovine serum albumin), hemiphosphorylated adapters, double-stranded, blunted cDNA, and 5 units of T4 DNA ligase in 20 µl total volume. The mixture is incubated overnight at 15° C. The ligation of blunt ends can be enhanced by the addition of PEG 8000; however, polyethylene glycol inhibits phage packaging reactions, and so, should be removed completely prior to these reactions. The ligation reaction is then loaded on a 1 ml bed volume Sephacryl S400 spin column (Promega), which is centrifuged at 800×g to remove excess adapters and adapter dimers. Alternative techniques which allow a more accurate size selection of cDNA product include agarose gel electrophoresis followed by capture and elution from cationic nitrocellulose (e.g. DEAE nitrocellulose), or recovery directly from harvested sections of low melt agarose.

The cDNA is quantified using scintillation, and the molar ends calculated (based on quantity and average size). The cDNA inserts are now ready for ligation into the vector of choice (constrained somewhat by the size of the inserts and the compatibility of the sticky end). Once again the ligation is performed as described above. With the use of hemiphosphorylated or unphosphorylated adapters, multiple insert cloning is unlikely, as only the vector has accessible phosphorylated ends.

The ligation reaction is then used for phage packaging, or diluted for chemical transformation or electroporation. Colonies or phage which appear are initially screened with blue/white color selection (alpha complementation), or with probes to abundant genes. In addition, random colonies or plaques are examined for insert size using PCR with primers which flank the cloning site, or by restriction digest analysis.

Using these general techniques libraries are constructed from cDNA made from CHO cells using the in vivo cDNA synthesis method. One of the libraries is made from the tRNA$_{wt}$-primed in vivo cDNA product (~1.9 kb) from CHO cells (see FIG. 8, lanes 4 and 8) which is size-selected on an agarose gel, using the DEAE nitrocellulose (NA45, S&S) capture/elution procedure, prior to cloning. Another library is made from the tRNA$_{PoLyU}$-primed in vivo cDNA product from CHO cells, which is size selected for cDNA between 4–10 kb using agarose gel electrophoresis.

The cDNA product (~1.9 kb) which appears in CHO cells with the tRNA$_{wt}$ primer may represent sequence-specific priming and synthesis from the conserved, moderately repetitive C-type and intracytoplasmic A-type particle (IAP) sequences found in all CHO cell lines examined (Anderson, K. P. et al., *Virol.* 181:305–311 (1991)). These species have extensive homology to the genome of murine leukemia virus.

Example 2

I. General Method for Assessing Suitability of Primers for in Vivo cDNA Synthesis Cellular reverse transcriptase cognate tRNA molecules, with modified ribonucleotide bases (see FIG. 2B) prime retroviral cDNA synthesis during viral replication. These molecules are not exclusively capable of priming in vivo cDNA synthesis, as evidenced by this invention and inferred from work previously done in vitro (Barat, C. et al., *Nucleic Acids Res.* 19:751–757 (1991); Weiss, S. et al., *Gene* 111:183–197 (1992); Kohlstaedt, L. A., and T. A. Steitz, *Proc. Natl. Acad. Sci. USA* 89:9652–9656 (1992)). In fact, fragments of synthetic tRNA molecules which lack base modifications are capable of annealing to RNA templates in vitro and directing in vitro cDNA synthesis from those templates (Weiss, S. et al., *Gene* 111:183–197 (1992)).

In Drosophila, reverse transcription in copia retrovirus-like particles occurs from cleavage and priming from the Drosophila tRNA$_i^{Met}$ molecule (Kikuchi, Y. et al., *Proc. Natl. Acad. Sci. USA* 87:8105–8109 (1990)). Therefore, it is apparent that synthetic polynucleotides which are truncated analogs of a reverse transcriptase enzyme's cognate tRNA primer molecule(s) may function as primers for this invention as well.

Determination of the suitability of a polynucleotide primer for in vivo cDNA synthesis reaction is straightforward. As defined previously, the primer will meet two (2) important criteria: Any oligonucleotide that is (a) capable of binding in vivo to an RNA template molecule and (b) acting as a primer for at least one reverse transcriptase enzyme such that synthesis of DNA complementary to that RNA template molecule occurs, is a legitimate primer for the in vivo cDNA synthesis of the present invention. Experiments which both quantitatively and qualitatively assess the suitability of a prospective primer may be performed, e.g., using Chinese hamster ovary (CHO) cells (see Example 1, above).

The in vivo assays consist of introduction of [$\alpha$-$^{32}$P] dCTP, putative primer, and Moloney murine leukemia virus reverse transcriptase into cells via electroporation. Controls for assessing the suitability of primers for in vivo cDNA synthesis can include the following negative controls:

1) Electroporation of [$\alpha$-$^{32}$P]dCTP alone.
2) Electroporation of [$\alpha$-$^{32}$P]dCTP along with the reverse transcriptase enzyme.

An actual primer test reaction can consist of:

3) Electroporation of [$\alpha$-$^{32}$P]dCTP along with the "candidate" polynucleotide primer and the reverse transcriptase enzyme.

A positive control reaction can consist of:

4) Electroporation of [$\alpha$-$^{32}$P]dCTP along with the modified tRNA$_{PoLyU}$ primer and the reverse transcriptase enzyme.

The hamster CHO cell line is obtained from the ATCC, and is maintained as described in Example 1. Prior to electroporation, the CHO cells are removed from monolayer culture using a trypsin/EDTA solution. The detached cells are counted, rinsed in PBS and resuspended in PBS at 1×10$^8$ cells/ml. The reaction components include the reverse transcriptase enzyme (1000 units), the tRNA primer (5 $\mu$g; or a molar equivalent of the candidate primer), and [$\alpha$-$^{32}$P]dCTP (50 $\mu$Ci), mixed in a total volume of 50 $\mu$l in reverse transcription buffer (BRL) containing DTT (10 mM), and incubated at room temperature for 10 minutes. Following preincubation, 0.5 ml of the CHO cells are added to the mixture, the cells mixed and immediately transferred to the electroporation cuvette. Electroporation is performed under the following conditions: 330V, 1000 $\mu$F and infinite resistance. After electroporation, 1 ml of warmed, CO$_2$-equilibrated Ham's medium (GIBCO) is added to the cuvette, the mixture is transferred to a plastic tube (Falcon #2059), and the mixture is then incubated for one hour at 37° C.

Following the incubation period, the cells are pelleted by centrifugation for 5 minutes at setting 5 in an Eppendorf Model 5415C microfuge (or the equivalent), and subjected to the extraction protocol described in Example 1, Section VI, and Cerenkov counts are obtained on the dried pellets.

The pellets are resuspended and aliquots are counted with scintillant. The products are electrophoresed on agarose/TAE gels with radiolabeled molecular weight standards. The gels are then stained with ethidium bromide, dried and examined by autoradiography.

Interpretation of Results

If the results of Cerenkov counts of incorporation of labeled deoxyribonucleotide into the final pellet from the experiment with the candidate polynucleotide primer exceeds the incorporation seen with the negative controls, and the incorporation seen with the positive control is approximately ten fold higher than the level seen with the negative control, then the test primer may be priming cDNA synthesis. However, the nature of the cDNA product(s) is very important and should be examined.

The second criteria, therefore, is a qualitative assessment of the product and is determined initially from the pattern and density of the autoradiographic signal obtained from test aliquots run, in parallel with radiolabeled molecular weight standards, on the agarose/TAE gel. If the polynucleotide primer is designed to anneal to an RNA template of heterogeneous size, or to a binding site which is a heterogeneous distance from the 5' end of the RNA template molecule, then one expects a heterogeneous population of cDNA products. If, however, the primer is designed to anneal to a specific homogeneous RNA template, a specific cDNA product should be produced (compare, for example, FIG. 8, lanes 4 and 5; and lanes 8 and 9). Therefore, both qualitative and quantitative parameters should be examined to determine the efficiency of a prospective primer.

Example 3

I. Generation of Sequence-specific in Vivo cDNA Synthesis Primers

The present invention also provides for sequence-specific in vivo cDNA synthesis reactions using a sequence-specific primer which is introduced into cells in combination with a compatible reverse transcriptase enzyme and, if desired, modified deoxynucleotide triphosphate or deoxynucleotide triphosphate analogs. These sequence-specific primers can be synthesized as transcripts prepared from a DNA template or by chemical means (e.g. on solid phase supports).

II. Chemical Synthesis Using Solid Phase Support

The ability to chemically synthesize unmodified oligonucleotides, and 2'-O-methyloligoribonucleotides in high yields on solid phase permits the present invention to be readily adapted for use in preparative, analytical and therapeutical applications. Synthetic techniques and reagents useful for modified oligoribonucleotide production (e.g. Sprout, B. S. et al., *Nucleic Acids Res.* 17:3373–3386 (1989), incorporated herein by reference), provide a number of embodiments which could not be achieved if the RNA primers are produced in vitro from a DNA template. For example, 2'-O-methyloligoribonucleotides are known to be resistant to RNase activity (Sprout, B. S. et al., (1989); Inoue, H. et al., *FEBS Lett.* 215:327–330 (1987)). Therefore, the use of these modified RNA molecules as primers for an in vivo cDNA synthesis reaction, in place of oligoribonucleotides, results in a resistance to RNase H-catalyzed removal of the initial cDNA synthesis primer (including any existing modifications). These primers can then be biotinylated, $^{32}$P-labeled, or contain sequence elements such as restriction sites which will be copied and incorporated during second-strand cDNA synthesis following base-catalyzed hydrolysis of the original template (the 2'-O-Methyl primer will protect the annealed complementary portion of the original RNA template as well). These modifications do not appear to disrupt the ability of the primers to associate with proteins (Sprout, B. S. et al., (1989)), and the modified oligoribonucleotides anneal with the expected specificity. The elimination of the 2'-OH group renders an RNA primer more resistant to base-catalyzed (nucleophilic) attack on the neighboring 3,'5'-phosphodiester bond, and it is resistant to a variety of ubiquitous RNases.

III. Transcription from Sequence-specific DNA Template

One embodiment capable of producing the desired sequence-specific tRNA primer consists of in vitro transcription from a DNA template, generally as follows:

The initial template for the production of a expression cassette, encoding a sequence-specific tRNA primer, can be the pUC18-T7tRNA$_{wt}$ vector construct. This construct encodes the tRNA$_{wt}$ molecule (see FIGS. 2B and 3A). The first of two primers will anneal to sequences which lie in the pUC18 vector 5' to the T7 promoter sequence (see FIG. 4) and extend in the 3' direction toward the T7 promoter sequence. A commercially available primer has been used in this manner in the amplification of the pUC18-T7tRNA$_{PolyU}$ expression cassette.

Figure 4:
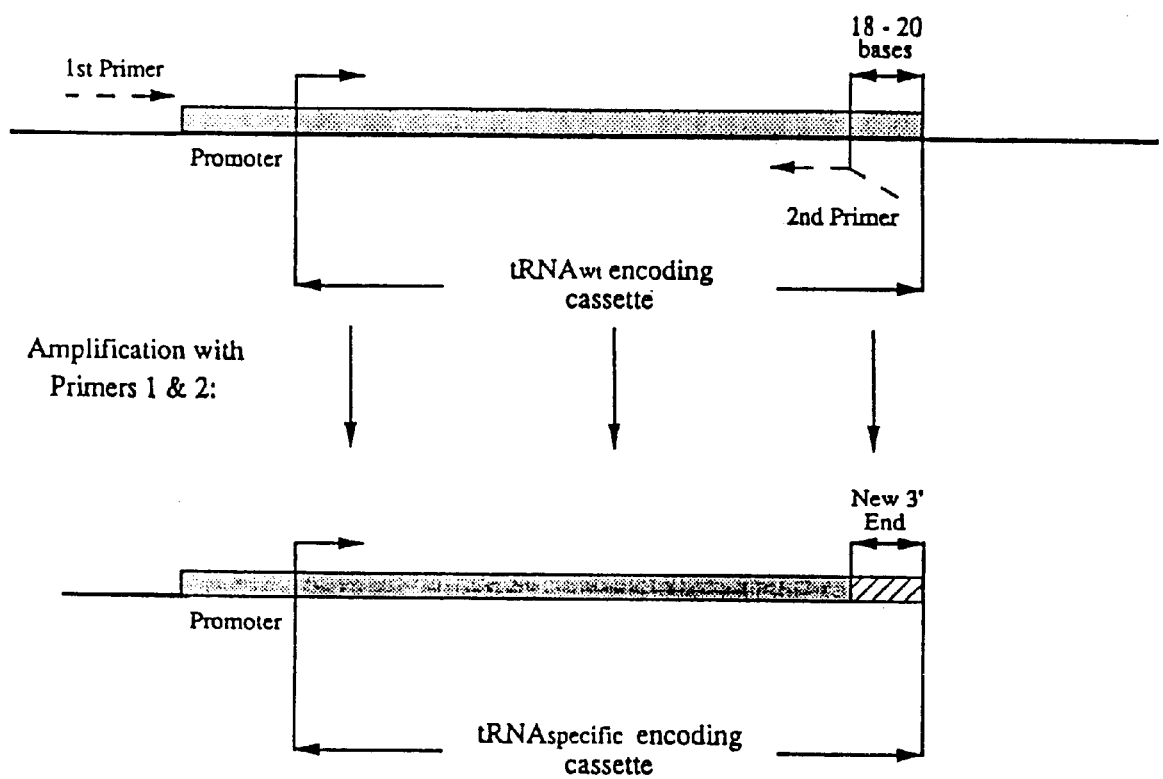
FIG. 4 depicts the steps involved in the amplification-mutagenesis of the tRNA-encoding promoter-tRNA cassette, wherein the first and second primers are represented by dashed lines with arrows delineating the 5' to 3' orientation, the second primer is represented by a bent dashed line to illustrate the inability of 5' bases to anneal to uncomplimentary bases in the initial template DNA molecule, and the bottom schematic represents the amplified and modified transcription cassette in which the 3'-most bases have been changed to the prescribed sequence encoded in the second primer, and the 3' end of the cassette is truncated at the end of this second primer sequence.

The second primer will desirably include bases at the 5' end of the primer which are complementary to a sequence in the RNA template of the in vivo cDNA synthesis reaction (e.g. an RNA template of known sequence), but are not complementary to the sequence of the initial DNA template (see FIG. 4). The remaining bases in the primer will be complementary to bases in the DNA template which are a like distance from the precise 3' end of the encoded tRNA template in the pUC18-T7tRNA$_{wt}$ DNA vector, and extend in the 3' direction toward the T7 promoter sequence (i.e. if 20 bases at the 5' end of this second primer are complementary to the RNA target for in vivo cDNA synthesis, then the remaining bases will be complementary to bases in the encoded T7tRNA$_{wt}$ DNA starting 20 bases from the 3' end). This situation is represented in FIG. 4.

Using these two primers in a PCR, the tRNA primer encoded in the amplified DNA T7 expression cassette is modified during the amplification process, from the initial tRNA$_{wt}$ template, to the desired tRNA$_{specific}$ template (see FIG. 4). Concomitantly, the 5' base of the second primer defines the 3' boundary of the resultant tRNA$_{specific}$ encoding cassette. This cassette produces a tRNA$_{specific}$ molecule with a 3' end which is complementary to both the 5' sequence encoded in the second PCR primer, and the RNA target for the in vivo cDNA synthesis reaction (see FIG. 4).

The PCR is performed in 20 µl volumes according to the following conditions: PCR buffer: 67 mM Tris (pH 9.2 at 25° C.), 16.6 mM (NH$_4$)$_2$SO$_4$, 1.5 mM MgCl$_2$; 50 ng of each primer, approximately 1×10$^8$ molecules of the pUC18-tRNA$_{wt}$ construct, and 250 µM concentrations of each of the deoxynucleotide triphosphates. The reaction mixtures are heated to 100° C. for 3 minutes, then cooled to 15° C. The tubes are centrifuged briefly to collect the contents, then 1 unit of Taq polymerase and a drop of mineral oil are added to each 20 µl reaction. The reaction is performed in 40 cycles with the following regimen: 1 minute at 94° C.; then 1 minute at 55° C. The products are pooled from 5 reactions, blunted with the Klenow fragment, extracted to remove protein and traces of mineral oil, and EtOH precipitated using standard protocols. The fragments are resuspended in 1 mM Tris-chloride (pH 8.0), 0.1 mM EDTA and an aliquot is examined on a 2% agarose/TAE gel with known size standards to verify size and to quantify. Typical yields are expected to be approximately 500 ng to 1 µg of product for each 20 µl reaction.

The tRNA$_{specific}$ molecule is then produced in an in vitro transcription reaction in a manner similar to that used for the production of tRNA$_{PolyU}$, above. Briefly, to RNase-free eppendorf tubes the following components are added at 25° C.: 80 mM Hepes-KOH (pH 7.5), 12 mM MgCl$_2$, 20 mM DTT, 5 mM dNTPs, 2 mM spermidine; RNase-free dH$_2$O ; 50–100 µg/ml template DNA and 5 µl of [α-$^{32}$P]ATP (30 mCi; 3000 Ci/mmol; added in order to examine and quantify the products). The reaction components are mixed, and the reaction is then initiated with the addition of T7 RNA polymerase enzyme reaction mix (to a final concentration of 1200–1800 U/ml). The tubes are then incubated at 37° C. for 4 hours. RNase-free DNase is then added to the reactions, and the digestion of template DNA allowed to proceed for 15–30 minutes; at this point, small aliquots of the reaction mixture can be removed in order to determine the efficiency of incorporation (This can be achieved by cold trichloroacetic acid precipitation of an aliquot of the reaction mixture in the presence of an excess of RNase-free carrier DNA. The control for this experiment, total counts, is done on unprecipitated material from the same reaction mixture). To each of the reaction mixtures is then added 150 $\mu$l of RNase-free dH$_2$O and 20 $\mu$l of 3M NaOAc and the mixtures are extracted with an equal volume of phenol/CHCl$_3$ (pH 6.5), followed by CHCl$_3$. The products are precipitated with 2-propanol, the pellets rinsed, and the precipitate dried. The primer product is resuspended in RNase-free dH$_2$O, and an aliquot checked for size using autoradiographic exposure of a polyacrylamide/urea gel run with known size standards. The primer is purified and quantified prior to introduction into cells.

This approach allows direct amplification of DNA cassettes which are used for in vitro production of sequence-specific tRNA primers for use with the MoMuLV reverse transcriptase enzyme. The technique utilizes a single sequence-specific DNA primer, a 5' universal primer and a tRNA$_{wt}$ DNA template for cassette amplification.

Example 4

I. Use of Sequence Specific Primers to Determine the Ratios of Splice Variants in Cells The ability to generate sequence-specific primers for use in the in vivo cDNA reactions enables an investigator to take a real time "snapshot" of the transcription patterns which exist in a target cell or tissue. Care in the preparation of the target cells for this analytical use of the in vivo cDNA synthesis technology is, perhaps, more important than for simple preparative use (e.g. cDNA library construction), and real assessment of the type of RNA primer, the mode of primer-reverse transcriptase (and, perhaps modified deoxynucleotide triphosphate, or analog) and delivery should be carefully considered. Many alternatives exist for delivering the primer/enzyme complex and a representative selection have been outlined above.

One technique for the manufacture of a DNA cassette which allows in vitro production of the sequence-specific primer is outlined in Example 3, above.

Following such synthesis, the primer product is resuspended in RNase-free dH$_2$O, and an aliquot checked for size using autoradiographic exposure of a polyacrylamide/urea gel run with known size standards. The primer is purified and quantified prior to introduction into cells.

An alternative and more direct approach is to chemically synthesize the RNA primer on solid phase support, generally as described in Example 3, Section II. This approach allows the direct synthesis of the sequence-specific primer, as well as providing an opportunity to incorporate modified stable ribonucleic acid analogs which would be useful for detection, purification and/or modification of the cDNA products (e.g. $^{32}$P-labeling, biotinylation, and/or sequence incorporation, respectively).

The cells are prepared in a manner which allows a minimum of perturbation to the desired conditions, and a delivery system is employed which is assessed to be the best at maximizing the speed of delivery of the reaction components, and minimizing stress to the cells or tissue.

In one such embodiment, the sequence-specific primer, reverse transcriptase enzyme, and [$\alpha$-$^{32}$P]dCTP are incubated together briefly in vitro (as described in Example 1, above), prior to addition to the cells or tissue. Following introduction to the cells or tissue, the cells or tissue is incubated under conditions which permit the synthesis of DNA molecule(s) which are complementary to the specific RNA template. The controls for this reaction include the following:

1) Delivery of [$\alpha$-$^{32}$P]dCTP alone.
2) Delivery of [$\alpha$-$^{32}$P]dCTP along with the reverse transcriptase.
3) Delivery of [$\alpha$-$^{32}$P]dCTP along with in vitro-transcribed "wild type" primer and the appropriate reverse transcriptase enzyme.

Following extraction and purification as described, above, the cDNA products can be qualitatively examined by autoradiographic analysis of gels run with appropriate radiolabeled size standards. In addition, the specific products can be quantified by scanning autoradiographs of analytical electrophoretic gels or by liquid scintillation counting of bands excised from preparative electrophoretic gels. The PCR can be used to detect any cDNA which is produced from unprocessed RNA template.

Example 5

I. Use of Multiple Sequence Specific Primers to Determine Ratios of Gene Transcripts in Cells The ability to generate sequence-specific primers for use in the in vivo cDNA reactions also enables one to use a real time "snapshot" of the target cell transcription patterns to detect differential transcription patterns and transcript levels, which are associated with numerous disease states. It is desirable from both a diagnostic and research perspective to identify the levels of various oncogene transcripts, in relation to the levels of an internal control transcript (e.g. a "housekeeping" gene). PCR has been used for this purpose in the past and is, at best, unreliable and biased due to problems which occur during amplification (Gilliland, G., et al. (1990)).

Consideration for the use of the invention in this manner, and techniques for the manufacture of DNA cassettes which allow in vitro production of the sequence-specific primers is outlined in Examples 3 and 4, above. A desirable approach in this embodiment is to chemically synthesize the RNA primers on solid phase support, generally as described in Example 3, Section II. This approach allows the direct synthesis of the distinct sequence-specific primers, and provides an opportunity to incorporate distinct modified ribonucleic acid analogs into each primer, which would be useful for differential detection, purification and/or modification of the cDNA products (e.g. $^{32}$P-labeling, biotinylation, and/or sequence incorporation, respectively).

Following such synthesis, distinct probe and control primer products are resuspended in RNase-free dH$_2$O, and aliquots are checked for size using autoradiographic exposure of a polyacrylamide/urea gel run with known size standards. The primers are purified and quantified prior to co-introduction into the target cells or tissues.

The cells are prepared in a manner which allows a minimum of perturbation to the desired conditions, and a delivery system is employed which is assessed to be the best at maximizing the speed of delivery of the reaction components, and minimizing stress to the cells or tissue.

In one such embodiment, an oncogene sequence-specific primer and an actin sequence-specific primer are utilized as probe primer and control, respectively. These distinct primers, reverse transcriptase enzyme, and [α-$^{32}$P]dCTP are incubated together briefly in vitro (as described in Example 1, above), prior to addition to the cells or tissue. Following introduction, the cells or tissues are incubated under conditions which permit the synthesis of DNA molecule(s) which are complementary to the specific RNA templates. The controls for this reaction include the following:

1) Delivery of [α-$^{32}$P]dCTP alone.
2) Delivery of [α-$^{32}$P]dCTP along with the reverse transcriptase.
3) Delivery of [α-$^{32}$P]dCTP along with the primer for one of the desired RNA templates and the appropriate reverse transcriptase enzyme.
4) Delivery of [α-$^{32}$P]dCTP along with the primer for each additional desired RNA template and the appropriate reverse transcriptase enzyme.

Following extraction and purification as described, above, the cDNA products can be qualitatively examined by autoradiographic analysis of gels run with appropriate radiolabeled size standards. In addition, the identity of specific products can be confirmed using, e.g., biotinylated molecular weight standards, and the gels can be transferred and Southern blots examined using a streptavidin/alkaline phosphatase conjugate system (e.g. the BluGENE System, Bethesda Research Laboratories, Gaithersburg, Md.).

Example 6

I. Use of Sequence Specific Primers to Clone Members of a Specific Gene Family

The ability to generate sequence-specific primers for use in the in vivo cDNA reactions enables an investigator to selectively produce cDNA from RNA templates which contain a specific sequence.

One technique for the manufacture of a DNA cassette which enables production of the sequence-specific primer in vitro is outlined in Example 3, above, and can be used as described. The primer is purified and quantified prior to introduction into cells.

A more direct alternative is to use the solid phase chemical synthesis techniques as described in Example 3.

The cells are prepared in a manner which allows a minimum of perturbation to the desired conditions and a delivery system is employed which is assessed to be the best at maximizing the speed of delivery of the reaction components, and minimizing stress to the cells or tissue. Some of these alternatives are outlined in the Detailed Description of the Invention, above.

Initially an analytical protocol is followed. If products of an expected size or size distribution are obtained, then preparative cDNA synthesis reaction(s) can be conducted.

For an analytical assessment of the primers and technique [α-$^{32}$P]dCTP can be included to rapidly investigate both quantitatively and qualitatively the results of the in vivo cDNA synthesis reaction.

In one experimental scheme, the sequence-specific primer, reverse transcriptase enzyme, and [α-$^{32}$P]dCTP are incubated together briefly in vitro, as described in Example 1, above, prior to addition to the cells or tissue. Following introduction to the cells or tissue, the cells or tissue is incubated under conditions which permit the synthesis of DNA molecule(s) which are complementary to the specific RNA template. The controls for this reaction might include the following:

1) Electroporation of [α-$^{32}$P]dCTP alone.
2) Electroporation of [α-$^{32}$P]dCTP along with the reverse transcriptase.
3) Electroporation of [α-$^{32}$P]dCTP along with in vitro-transcribed "wild type" primer and the appropriate reverse transcriptase.

Figure 8:
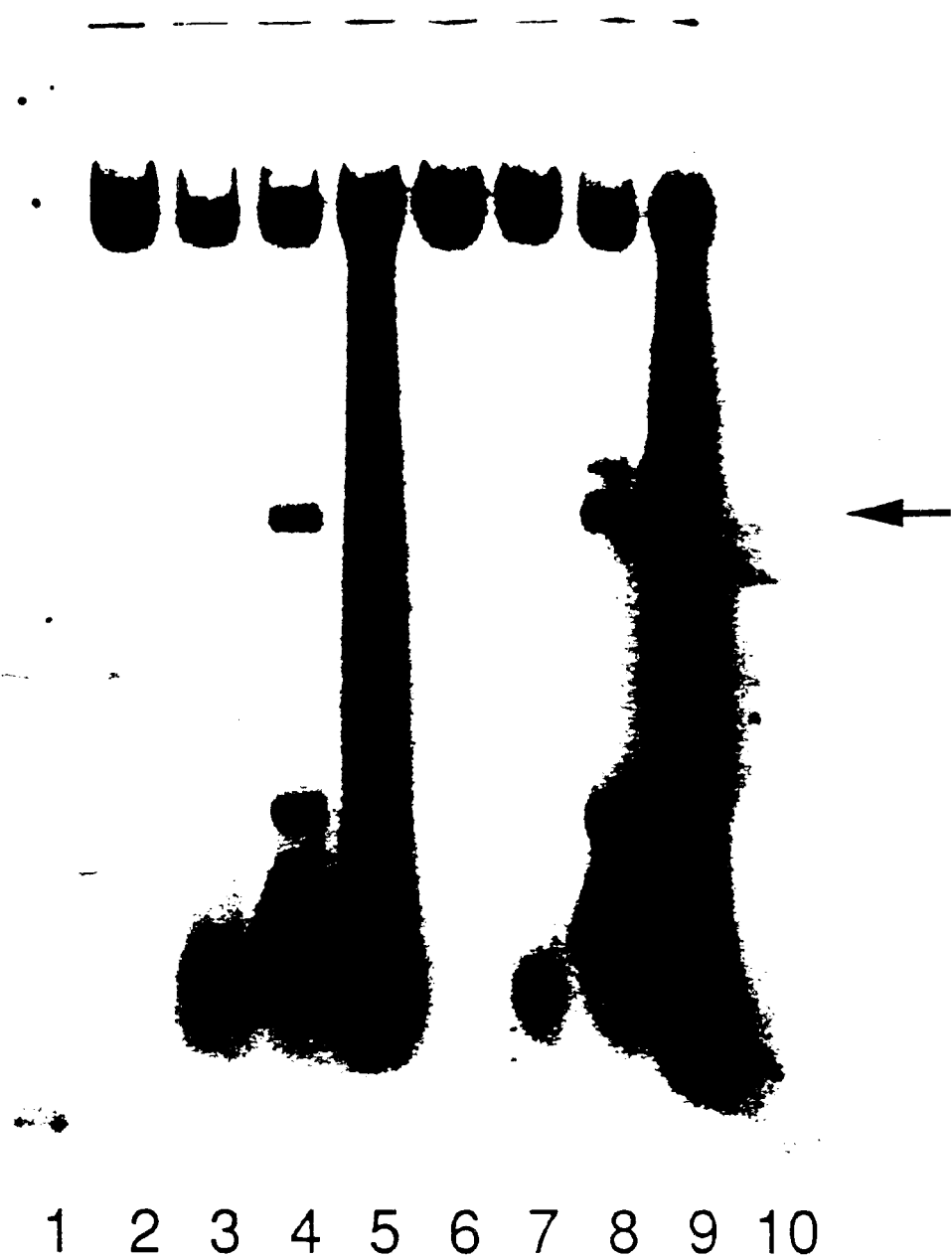
FIG. 8 is a photographic reproduction of an autoradiograph of the gel image depicted in FIG. 6.
Figure 9:
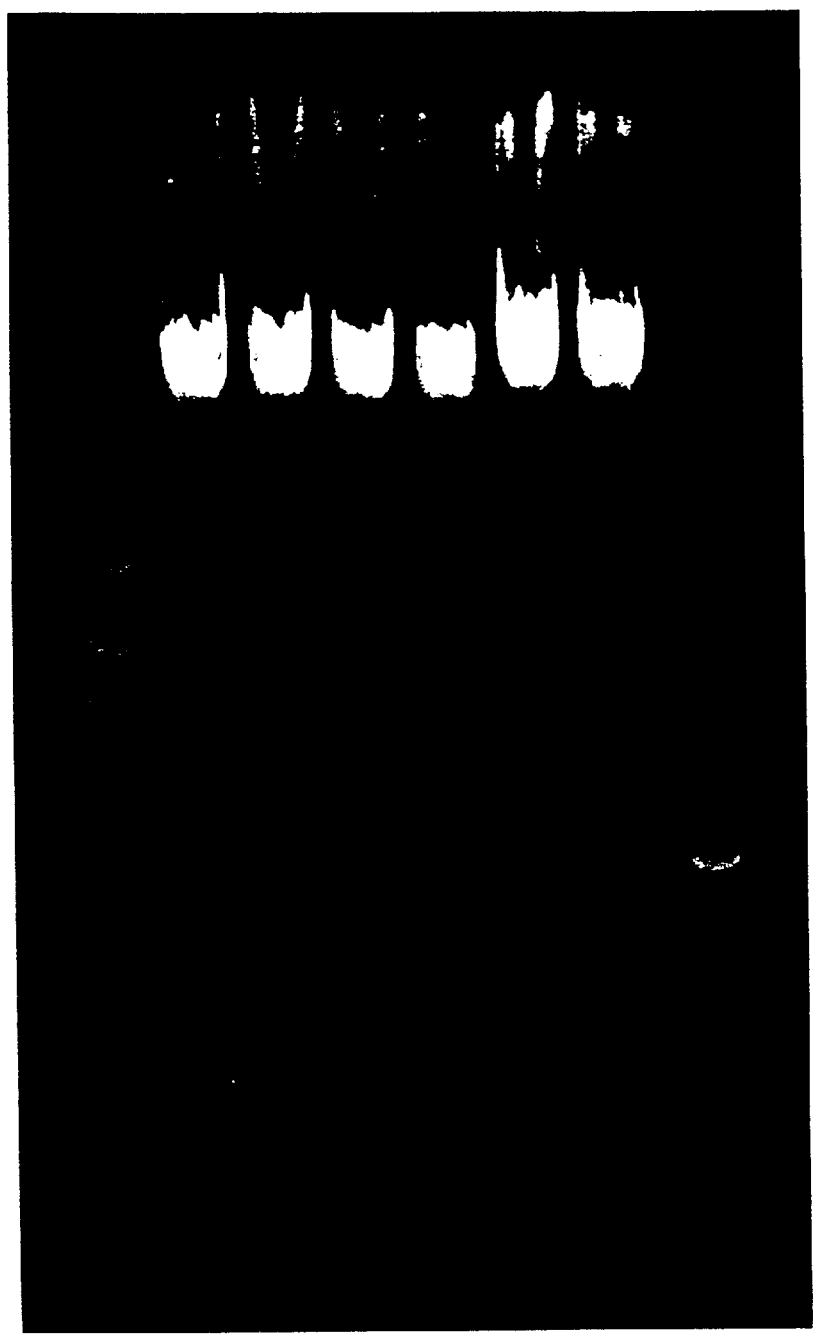
FIG. 9 is a photographic reproduction of an ethidium bromide stained 1% agarose/TAE gel of in vivo cDNA products from Hamster (CHO) cells, in which lanes 1 and 8 represent a 1 kb ladder (BRL), lanes 2 and 3 represent control ([$\alpha$-$^{32}$P]dCTP+reverse transcriptase+tRNA$_{wt}$), lanes 4 and 5 represent experimental with modified tRNA primer ([$\alpha$-$^{32}$P]dCTP+reverse transcriptase+tRNA$_{PoLyU}$), and lanes 6 and 7 represent control ([$\alpha$-$^{32}$P]dCTP+reverse transcriptase+oligo(dT) (5 $\mu$g). In this example, the samples in lanes 3, 5, and 7 are treated with S1 nuclease.

Following extraction and purification as described, above, the cDNA products can be qualitatively examined by ethidium stained gels (see FIG. 7, lanes 4 and 8), or autoradiographic analysis of gels run with appropriate radiolabeled size standards (see FIG. 8, lanes 4 and 8). In addition, the level of incorporation can be determined by measurement of Cerenkov counts, or, following resuspension, by liquid scintillation counting of aliquots.

Following an analytical examination, similar reactions can be performed in the absence of the radiolabeled deoxynucleotide triphosphates (or with a reduced amount—to use as a tracer). The number of reactions needed to obtain the desired product(s) is determined by the previous analytical reactions.

The cDNA products from the reactions, above are cloned into vectors using accepted cloning techniques, as described in Example 1, Section IX.

Example 7

I. Use of Sequence-specific Primers and Four Fluorescent Dideoxynucleotide Analogs for Direct Sequencing of in Vivo cDNA Products A series of fluorescent dideoxynucleotide triphosphate analogs have been developed which have discrete fluorescent emission spectra, and are readily incorporated into DNA by reverse transcriptase enzymes (Prober, J. M., et al. (1987)). Each analog substitutes for a specific dideoxynucleotide chain-terminating base, and is incorporated into DNA in a template-directed manner. The ability to incorporate modified dideoxynucleotide analogs in vivo, directed from a sequence-specific primer, allows direct sequencing of any RNA template which contains the desired 3' sequence, and is present in a detectable amount.

There are likely to be some 15,000 different transcripts in a typical eukaryotic cell (Sargent, T. D. (1987). If a sequence-specific primer is produced with a polyuridylic acid stretch near the 3' end (designed to position the primer at the polyadenylated 3' end of the RNA template), followed directly with a specific 8 base sequence at the extreme 3' end, then only one cDNA product is likely to be produced ($0.25^8=1/65,536$) from the mRNA templates present in a eukaryotic cell.

Introduction of this modified tRNA primer (produced in a manner similar to the techniques described in Example 3), along with the compatible reverse transcriptase enzyme, the bio-11-dUTP deoxynucleotide analog (if the primer is not biotinylated; see Example 3; Example 8, below), and the four (4) fluorescent base- and spectra-specific dideoxynucleotide triphosphate analogs (Prober, J. M. et al. (1987)) results in a nested series of cDNA synthesis products which are extracted and concentrated using, e.g., an avidin-coated polystyrene (Baxter Healthcare, Mundelein, Ill.) or streptavidin-linked bead, eluted by heating in gel loading buffer, and electrophoresed on an analytical denaturing polyacrylamide gel. The gel apparatus is attached to a laser-equipped, spectra-discriminating fluorescence excitation and detection device. This allows direct DNA sequencing of expressed genes from an organism without prior cloning, or even preexisting knowledge of sequence. Of course, a similar preliminary experiment (with the inclusion of [α-$^{32}$P]dCTP, and the absence of the dideoxy chain-terminating analogs) can be performed in order to confirm that a single cDNA species is produced with the primer. This can be confirmed following extraction by autoradiography on an agarose/TAE electrophoretic gel.

An alternative technique for obtaining DNA sequence information directly from in vivo cDNA products without cloning is to gel-purify specific cDNA bands on low-melt agarose electrophoretic gels. These products may be directly sequenced using currently accepted sequencing techniques, including solid-phase sequencing if a biotinylated primer is used (Syvanen, A-C. et al. *FEBS Lett.* 258:71–74 (1989)). The sequence-specific tRNA primer molecule used for cDNA synthesis suggests a sequencing primer which is used for the reaction.

Yet another useful approach is to introduce [$\alpha$-$^{32}$P] dNTPs, a biotinylated, sequence-specific tRNA primer, the reverse transcriptase, and one of the four (4) dideoxynucleotide triphosphate chain-terminating molecules into the target cell. In this manner, four separate introductions are performed, each introducing a different chain-terminating dideoxynucleotide base. The cells are then incubated for the time, and in a manner which allows incorporation. The nested cDNA products are extracted and concentrated using, e.g., an avidin-coated polystyrene (Baxter Healthcare, Mundelein, Ill.) or streptavidin-linked bead, and eluted from the bead by heating in sequencing gel loading buffer just prior to loading a sequencing gel. The sequence can then be determined by autoradiography.

In addition, these techniques permit a direct approach to determining the 5' sequence of clones where information concerning the 3' sequence is available. The choice of a specific 18 base primer sequence will permit specific sequencing in vivo without the time and difficulty of cloning the cDNA product.

Example 8

I. Incorporation of Biotinylated dUTP During in Vivo cDNA Synthesis Reactions

The ability to incorporate deoxynucleotide analogs into the in vivo cDNA product allows the preparation and recovery of biotinylated cDNA which can be useful in a number of important areas. Specific biotinylated deoxynucleotide analogs are appropriate for specific experiments, and many candidate substrates exist (Klevan, L., and Gebeyehu, G., *Meth. Enzymol.* 154:561–577 (1987)). The following Example utilizes one approach and should not be construed as defining or limiting alternative methods or techniques for biotinylation of the in vivo cDNA product. Alternatives such as biotinylation of the RNA primer (see Example 3) or incorporation of the dATP analog N$^6$-(-aminoalkyl)dATP during the in vivo cDNA synthesis reaction, followed by reaction of the amine-labeled cDNA with a reporter molecule, biotin-N-hydroxysuccinimide ester, after extraction and purification, are useful approaches.

The hamster CHO cell line is obtained from the ATCC, and maintained as recommended. Prior to electroporation, the CHO cells are removed from monolayer culture using a trypsin/EDTA solution. The detached cells are counted, rinsed in phosphate buffered saline and resuspended in phosphate buffered saline at $1\times10^8$ cells/ml. The reaction components are reverse transcriptase enzyme (1000 units), the tRNA primer (5 $\mu$g; can be either sequence-specific, or a general primer, e.g. tRNA$_{PolyU}$), and bio-11-dUTP (0.03 mM or 0.3 mM final) which are mixed in a total volume of 50 $\mu$l in reverse-transcription buffer (BRL) containing DTT (10 mM), and incubated at room temperature for 10 minutes. Following preincubation, 0.5 ml of the CHO cells are added to the mixture, the cells mixed and immediately transferred to a chilled 0.4 cm electroporation cuvette. Electroporation is performed under the following conditions: 330 volts (V), 1000 microfarads ($\mu$F) and infinite resistance. After electroporation, 1 ml of warmed, $CO_2$-equilibrated Ham's medium (GIBCO) is added to the cuvette, the mixture is transferred to a plastic tube (Falcon #2059), and the mixture is then incubated for one hour at 37° C.

Following the incubation period, the cells are pelleted by centrifugation for 5 minutes at setting 5 in an Eppendorf Model 5415C microfuge (or the equivalent), and the cDNA product is recovered as described in Example 1. The biotinylated cDNA pellets are resuspended, and the products electrophoresed on agarose/TAE gels. These gels can be run with biotinylated molecular weight standards, and the gels can be transferred and the Southern blot examined using a streptavidin/alkaline phosphatase conjugate system (e.g. the BluGENE System, Bethesda Research Laboratories, Gaithersburg, Md.).

The products can be purified and extracted from preparative agarose gels and used for probes in electron microscopy (using streptavidin-gold), for in situ hybridization (using streptavidin/alkaline phosphatase detection system (Chan, et al. (1985)), subtractive library construction, as well as other preparative, analytical and therapeutic purposes.

Example 9

I. Use of Biotinylated in Vivo cDNA in Subtractive Library Construction

The ability to increase the relative frequency of induction-specific, or cell or tissue-specific messages prior to the construction and screening of a cDNA library, is of great strategic benefit, and often the only hope of identification and recovery of genes which are represented by mRNAs of low abundance (Hedrick, S. et al., *Nature* 308:149 (1984)). The previously known subtraction techniques utilizes a separation strategy whereby single-stranded cDNA (produced from mRNA selected from the desired cells, tissues or conditions) is annealed to an excess of mRNA extracted from alternate cells, tissues or conditions. The heteroduplex molecules are separated from the single-stranded cDNA (and mRNA) using hydroxylapatite, or other selective matrices.

The ability to incorporate deoxynucleotide analogs into the in vivo cDNA product allows the preparation and recovery of biotinylated cDNA.

One of the uses of the biotinylated cDNA product of this in vivo incorporation is in subtractive library construction. This alternative technique of library construction is superior to the prior art, in that both the desired template, and the subtracting template molecules are cDNA, allowing a stability during the hybridization and selection process not previously possible. In addition, the cDNA product is produced from a smaller initial number of cells, with a fidelity and processivity which may exceed the quality of products produced in vitro.

The incorporation reaction can be performed as described in Examples 3 or 8, or by alternate means. The biotinylated cDNA is produced in cells or tissue which is grown under conditions other than those of the desired cDNA library. The extracted and isolated biotinylated cDNA product is treated with S1 nuclease to cleave any hairpin structure(s) which might link first-strand product from second-strand product; separated from any contaminating sheared genomic DNA by column chromatography or gel electrophoresis, and annealed to approximately 1/30 the quantity of nonbiotinylated cDNA product which was produced from the desired cell or tissues, or from cells or tissues grown under alternate, desired conditions (and similarly separated from genomic DNA contaminants). Routine hybridization conditions are: 120 mM $NaH_2PO_4$ (pH 6.8), 820 mM NaCl, 1 mM EDTA, 0.1% SDS, with the final DNA concentration at approximately 5 mg/ml. The reaction mixture is heated to 90° C. for 5 minutes, then maintained at 65° C. for 12–18 hours. The reaction is diluted in phosphate buffer (120 mM $NaH_2PO_4$, pH 6.8), and the biotinylated cDNA, with annealed common cDNA sequences, is isolated on a streptavidin column. The flow-through cDNA fraction is concentrated by ethanol precipitation and cloned using accepted methods and techniques (Sambrook, (1989)).

Example 10

I. Incorporation of Fluorescent Deoxynucleotide Analog(s) During in Vivo cDNA Synthesis Directed from an HIV Sequence-specific Primer to Identify HIV-infected CD4 Lymphocytes There are a number of commercially available fluorescent deoxynucleotide triphosphate analogs which have discrete fluorescent emission spectra and are readily incorporated into DNA by polymerase enzymes. Each analog is incorporated into DNA in a template-directed manner. The ability to incorporate these modified deoxynucleotide analogs in vivo, directed from a sequence-specific primer, allows a rapid and direct method for screening for HIV-infected CD4 lymphocytes using flow cytometry. This screening can be utilized for analytical purposes, or can be used to separate infected from uninfected CD4 lymphocytes, thereby providing a therapeutic approach to HIV-positive individuals.

A human immunodeficiency virus, type I sequence-specific primer for use in the present in vivo cDNA synthesis invention is made with an appropriate HIV-specific sequence. One such PCR primer is prepared, based on the sequence of the SK69 primer (Ou, C—Y et al., *Science* 239:295–297 (1988); Zack, J. A. et al., Cell 61:213–222 (1990)) corresponding to the env region of HIV, as follows (SEQ ID NO. 9):
5'-CTGTTGCAAC TCACAGTCTG GAACCCGGGA CCTCTCGCAC CCC
which can be used in PCR as described in Example 3 to generate a DNA cassette for the production of the HIV-specific tRNA primer.

Alternatively, a PCR primer can be based on the M666 primer of Watson & Wilburn (1992), corresponding to the $U_3$ region of LAV-$1_{BRU}$, as follows (SEQ ID NO. 10):
5'-GGGGAGTGGC GAGCCCTCTT GAACCCGGGA CCTCTCGCAC CCC The purified, examined and quantitated primer is then introduced into cytokine-activated (Poli, G. and A. S. Fauci, *AIDS Res. Hum. Retroviruses* 8:191 (1992)) lymphocytes (either fractionated, or unfractionated) utilizing appropriate technique(s) (among them, electroporation and cationic lipid-mediated delivery), along with MoMuLV reverse transcriptase enzyme, and fluorescent deoxynucleotide triphosphate analog(s). The cells are incubated under conditions and for a time necessary to produce cDNA to any existing HIV-specific RNA template present in the target cells. A control reaction can be performed on a similar, uninfected cell population.

The cells are washed and then, if desired, incubated on ice for 30 minutes with an antibody directed to the CD4 molecule (e.g. OKT4 from the ATCC), washed and incubated with FITC-labeled F(ab')$_2$ goat anti-mouse IgG. The cells are then washed again, prepared and screened by Fluorescence Activated Cell Sorting (FACS) using parameters (e.g. gating for cell size, fluorescence and threshold spectra) necessary to excite and screen for the incorporated fluorescent tag(s). Appropriate parameters can be determined using the negative control cell populations.

If the experiment is done with the inclusion of an anti-CD4 antibody (with appropriate alternate emission wavelength), these techniques allow both quantitation and separation of HIV-infected lymphocytes.

Alternatively, following in vivo cDNA synthesis, the cells can be fixed and permeabilized prior to examination; however, this is primarily an analytical embodiment, rather than a preparative one.

Thus it has been shown that the present invention provides beneficial methods and compositions for cDNA synthesis. It has been shown that in vivo cDNA synthesis reaction works efficiently, as evidenced by: (a) The incorporation of deoxynucleotides into a polynucleotide fraction of a varying size—as is predicted for cDNA synthesis reactions with a heterogeneous mRNA template population (see FIG. 6, lanes 5, 9, 11, and 12; FIG. 8, lanes 5 and 9); (b) The reaction depends on the inclusion of both reverse transcriptase enzyme and primer (FIG. 6: compare lanes 3 and 5; lanes 7 and 9; FIG. 8: compare lanes 3 and 5; lanes 7 and 9); (c) The reaction products are resistant to ribonuclease A treatment (even when the ribosomal RNA fraction, present in the extracts, is digested to completion (in FIGS. 5 and 6: compare lanes 5 and 11; lanes 9 and 12); and, (d) The heterogeneous nature of the products are dependent on the inclusion of a modified tRNA primer which is designed to anneal and prime off a heterogeneous cellular population of polyadenylated messenger RNA vs. reactions where a single prominent cDNA product is obtained (~1.9 kb) when a specific primer is utilized (FIGS. 7 and 8: compare lanes 4 and 5; and lanes 8 and 9).

It has also been shown that the in vivo cDNA synthesis reaction works successfully with a number of unrelated types of cells (In all eukaryotic cells attempted: Sf9—insect cells; CHO cells—Hamster cells; HeLa cells—Human cells).

And it has been shown that the products of the in vivo cDNA synthesis reactions are double-stranded polynucleotides—most probably double-stranded DNA, as evidenced by: (a) The treatment with S1 nuclease results in no appreciable degradation of the reaction products (see FIG. 10: compare lanes 2 and 3; lanes 4 and 5); (b) The treatment of the products with ribonuclease H followed by treatment with S1 nuclease appears to result in no discernible degradation of the reaction products; (c) The in vivo cDNA synthesis reaction does not work when a reverse transcriptase enzyme which lacks ribonuclease H activity is used. The success of the in vivo cDNA synthesis reaction appears to depend, to some extent, on the ability of the reverse transcriptase to digest away the original RNA template; this is a block to second strand synthesis, both in vitro, and in retroviral replication (Tanese, N., et al., *J. Virol.* 65:4387–4397 (1991)); and (d) The products are clonable using conventional cloning techniques.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the appended claims.

What is claimed is:

1. A method for synthesizing a complementary DNA copy of an RNA template molecule which method comprises:
   (a) providing at least one polynucleotide molecule which functions as a primer molecule for at least one reverse transcriptase enzyme and which anneals in vivo to an RNA template molecule at a position other than a naturally-occurring retroviral primer binding site, wherein said polynucleotide molecule comprises a stem loop structure recognized by said reverse transcriptase enzyme;
   (b) providing at least one reverse transcriptase enzyme which initiates DNA synthesis in vivo using the polynucleotide molecule as a primer;
   (c) introducing the polynucleotide molecule into a viable target cell in the presence of the reverse transcriptase enzyme; and
   (d) incubating the target cell under conditions which permit the synthesis of a DNA molecule complementary to the RNA template molecule.

2. The method of claim 1 wherein the RNA template molecule comprises messenger RNA.

3. The method of claim 1 wherein the polynucleotide molecule comprises ribonucleic acid.

4. The method of claim 3 wherein the ribonucleic acid comprises a reverse transcriptase-cognate primer transfer RNA molecule.

5. The method of claim 4 wherein the reverse transcriptase-cognate primer transfer RNA molecule is modified so as to anneal to the 3' polyadenylic acid tail of a messenger RNA molecule.

6. The method of claim 5 wherein the modified reverse transcriptase-cognate primer transfer RNA molecule comprises a primer transfer RNA molecule modified at its 3' end with a polyribouridylic acid sequence.

7. The method of claim 6 wherein the modified primer transfer RNA molecule comprises a modified murine tRNA$^{Pro}$GGG molecule and wherein the reverse transcriptase is Moloney murine leukemia virus reverse transcriptase.

8. The method of claim 6 wherein the reverse transcriptase enzyme is Moloney murine leukemia virus reverse transcriptase and the modified reverse transcriptase-cognate primer transfer RNA molecule is a modified murine tRNA$^{Pro}$GGG molecule modified at its 3' end with a polyribouridylic acid sequence.

9. The method of claim 7 wherein the modified reverse transcriptase-cognate primer transfer RNA molecule comprises the sequence shown in SEQ ID No.: 7.

10. The method of claim 1 wherein the polynucleotide molecule is introduced into the viable target cell by electroporation.

11. The method of claim 1 wherein the reverse transcriptase enzyme is introduced into the viable target cell.

12. The method of claim 1 wherein the reverse transcriptase enzyme is synthesized within the viable target cell.

13. The method of claim 1 wherein the reverse transcriptase enzyme and the polynucleotide molecule are introduced separately into the viable target cell.

14. The method of claim 1 wherein the reverse transcriptase enzyme and the polynucleotide molecule are concurrently introduced into the viable target cell.

15. The method of claim 14 wherein the step of introduction of the reverse transcriptase enzyme and the polynucleotide molecule is performed by electroporation.

16. The method of claim 1 wherein the viable target cells are eukaryotic cells.

17. A polynucleotide molecule which anneals in vivo to an RNA template molecule at a position other than a naturally-occurring retroviral primer binding site and functions in vivo as a primer molecule for at least one reverse transcriptase enzyme, wherein said polynucleotide molecule comprises a stem loop structure recognized by said reverse transcriptase enzyme.

18. The polynucleotide molecule of claim 17 wherein the RNA template molecule comprises messenger RNA.

19. The polynucleotide molecule of claim 17 comprising a reverse transcriptase-cognate primer transfer RNA molecule.

20. The polynucleotide molecule of claim 17 wherein said molecule is capable of annealing in vivo to a 3' poly (A) tail of a messenger RNA molecule.

21. The polynucleotide molecule of claim 20 wherein said molecule comprises a primer transfer RNA molecule modified at its 3' end with a polyribouridylic acid molecule.

22. The polynucleotide molecule of claim 21 wherein said molecule comprises a modified murine tRNA$^{Pro}$GGG molecule modified at its 3' end with a polyribouridylic acid molecule.

23. The polynucleotide molecule of claim 22 wherein said RNA molecule comprises the sequence shown in SEQ ID No: 7.

24. A kit for synthesizing in vivo a complementary DNA copy of an RNA molecule, said kit comprising:
   (a) a preparation of a polynucleotide molecule, which molecule anneals in vivo to an RNA template molecule at a position other than a naturally-occurring retroviral primer binding site and functions in vivo as a primer molecule for at least one reverse transcriptase enzyme, wherein said polynucleotide molecule comprises a stem loop structure recognized by said reverse transcriptase enzyme; and
   (b) a preparation of at least one reverse transcriptase enzyme which initiates transcription in vivo from said polynucleotide molecule and which synthesizes a complementary DNA copy of the RNA template molecule.

25. The kit of claim 24 wherein the RNA template molecule is messenger RNA.

26. The kit of claim 24 wherein said polynucleotide molecule is a reverse transcriptase-cognate primer transfer RNA molecule.

27. The kit of claim 26 wherein said modified reverse transcriptase-cognate primer transfer RNA molecule comprises a modified murine tRNA$^{Pro}$GGG molecule modified at its 3' end with a polyribouridylic acid molecule and wherein the reverse transcriptase enzyme is Moloney murine leukemia virus reverse transcriptase.

28. The kit of claim 27 wherein the modified reverse transcriptase-cognate primer transfer RNA molecule comprises the sequence shown in SEQ ID No: 7.

29. The kit of claim 24 wherein the kit further comprises sufficient deoxynucleotide triphosphates to complete the synthesis of at least one complementary DNA copy of at least one endogenous RNA template molecule in a host cell.

30. The kit of claim 24 wherein the kit further comprises at least one deoxynucleotide triphosphate analog in an amount sufficient to render a complementary DNA molecule produced in a host cell capable of being detected.

31. The kit of claim 24 wherein the kit further comprises reagents for introducing the preparations into a target cell.

32. A DNA molecule comprising a first DNA sequence encoding a polynucleotide molecule which anneals in vivo to an RNA template molecule at a position other than a naturally-occurring retroviral primer binding site and functions as a primer molecule for at least one reverse transcriptase enzyme, wherein said polynucleotide molecule comprises a stem loop structure recognized by said reverse transcriptase enzyme.

33. The DNA molecule of claim 32 wherein the RNA template molecule is messenger RNA.

34. The DNA molecule of claim 32 wherein the polynucleotide molecule is a reverse transcriptase-cognate primer transfer RNA molecule.

35. The DNA molecule of claim 34 wherein the polynucleotide molecule comprises a modified primer transfer RNA molecule modified at its 3' end with a polyribouridylic acid molecule.

36. The DNA molecule of claim 35 wherein the DNA molecule comprises the sequence shown in SEQ ID No: 8.

37. The DNA molecule of claim 32 wherein the DNA molecule further comprises a promoter sequence operatively linked to the 5' end of the first DNA sequence, said promoter sequence capable of directing transcription of the first DNA sequence.

38. The DNA molecule of claim 37 wherein the promoter sequence is a promoter sequence at which an RNA polymerase can initiate transcription.

39. The DNA molecule of claim 37 wherein the first DNA sequence encodes a modified murine tRNA$^{pro}$GGG molecule modified at its 3' end with a polyribouridylic acid molecule.

40. The DNA molecule of claim 38 wherein the DNA molecule further comprises at least one restriction enzyme recognition site suitable for linearizing the DNA molecule at a point immediately 3' of the polyribouridylic acid molecule.

41. A recombinant DNA vector which comprises a nucleotide sequence encoding a polynucleotide molecule which anneals in vivo to an RNA template molecule at a position other than a naturally-occurring retroviral primer binding site and which functions as a primer molecule for at least one reverse transcriptase enzyme, wherein said polynucleotide molecule comprises a stem loop structure recognized by said reverse transcriptase enzyme.

42. The recombinant DNA vector of claim 41 wherein the RNA template molecule is messenger RNA.

43. The recombinant DNA vector of claim 41 wherein the polynucleotide molecule is a reverse transcriptase-cognate primer transfer RNA molecule.

44. The recombinant DNA vector of claim 43 wherein the polynucleotide molecule is a modified murine tRNA$^{pro}$GGG molecule modified at its 3' end with a polyribouridylic acid molecule.

45. A recombinant DNA vector which comprises a nucleotide sequence encoding a reverse transcriptase-cognate primer transfer RNA molecule, which molecule anneals in vivo to an RNA template molecule at a position other than a naturally-occurring retroviral primer binding site and which functions in vivo as a primer molecule for a reverse transcriptase enzyme, wherein said polynucleotide molecule comprises a stem loop structure recognized by said reverse transcriptase enzyme.

46. The recombinant DNA vector of claim 45 wherein the reverse transcriptase-cognate primer transfer RNA molecule is modified at its 3' end with a polyribouridylic acid molecule.

47. The recombinant DNA vector of claim 45 wherein the recombinant vector comprises the sequence shown in SEQ ID No: 8.

48. A transformed host cell containing the vector of claim 45.

49. The transformed host cell of claim 48 wherein said host cell is a bacterial cell.

50. A synthetic polynucleotide molecule which anneals in vivo to an RNA template molecule at a position other than a naturally-occurring retroviral primer binding site and functions in vivo as a primer for an DNA polymerase enzyme, wherein said polynucleotide molecule comprises a stem loop structure recognized by said DNA polymerase enzyme such that synthesis of a DNA molecule complementary to the RNA template molecule can occur.

51. The synthetic polynucleotide molecule of claim 50 which is capable of:

(a) annealing in vivo to an RNA template molecule; and (b) acting as a primer for an RNA-dependent DNA polymerase enzyme such that synthesis of a DNA molecule complementary to the RNA template molecule can occur.

52. A recombinant RNA molecule comprising: a modified tRNA molecule in which at least 3' ribonucleoside bases are replaced with ribouridyl bases and wherein the molecule has an activity of promoting in vivo reverse transcriptase polymerase activity on an RNA template molecule.

53. A recombinant RNA molecule which has an activity of promoting in vivo reverse transcriptase polymerase activity on an RNA template molecule by annealing to the template molecule at a position other than a naturally-occurring retroviral primer binding site, wherein said polynucleotide molecule comprises a stem loop structure recognized by said reverse transcriptase polymerase enzyme.

54. A method for producing in vivo a complementary DNA copy of an RNA template molecule of which at least a partial sequence is known comprising:

(a) providing a DNA molecule comprising a gene which encodes a promoter sequence operatively linked to a polynucleotide molecule which anneals in vivo to an RNA template molecule at a position other than a naturally-occurring retroviral primer binding site and functions as a primer for at least one reverse transcriptase enzyme, wherein said polynucleotide molecule comprises a stem loop structure recognized by said reverse transcriptase enzyme;

(b) providing a first nucleotide primer wherein said primer is homologous to a sequence located 5' to the end of the promoter sequence;

(c) providing a second nucleotide primer wherein said primer comprises a 3' sequence that is complementary to a 3' region of the polynucleotide molecule of step (a) joined to a 5' sequence that is complementary to a portion of the known RNA template molecule sequence;

(d) contacting said DNA molecule with said first and second primers;

(e) treating the mixture of step (d) under conditions and with reagents which permit the amplification of said cloned DNA molecule;

(f) treating at least one amplified DNA molecule produced in step (e) under conditions and with reagents which permit the production of an encoded RNA molecule;

(g) introducing the RNA molecule produced in step (f) into a viable target cell in the presence of at least one reverse transcriptase enzyme which initiates DNA synthesis using said RNA molecule as a primer; and (h) incubating the target cell under conditions such that a DNA molecule complementary to at least one RNA template molecule is produced.

55. The method of claim 54 wherein the RNA template molecule comprises messenger RNA.

56. The method of claim 54 wherein the polynucleotide molecule comprises ribonucleic acid.

57. The method of claim 56 wherein the ribonucleic acid comprises a reverse transcriptase-cognate primer transfer RNA molecule.

58. The method of claim 57 wherein the reverse transcriptase-cognate primer transfer RNA molecule is capable of annealing to the 3' polyadenylic acid tail of a messenger RNA molecule.

59. The method of claim 58 wherein the reverse transcriptase-cognate primer transfer RNA molecule comprises a modified primer transfer RNA molecule modified at its 3' end with a polyribouridylic acid sequence.

60. The method of claim 59 wherein the modified primer transfer RNA molecule comprises a modified murine tRNA$^{pro}$GGG molecule and wherein the reverse transcriptase is Moloney murine leukemia virus reverse transcriptase.

61. The method of claim 60 wherein the reverse transcriptase enzyme is Moloney murine leukemia virus reverse transcriptase and the modified reverse transcriptase-cognate primer transfer RNA molecule is a modified murine tRNA$^{pro}$GGG molecule modified at its 3' end with a polyribouridylic acid sequence.

62. The method of claim 61 wherein the modified reverse transcriptase-cognate primer transfer RNA molecule comprises the sequence shown in SEQ ID No.: 7.

63. The method of claim 54 wherein the RNA molecule of step (g) is introduced into the viable target cell by electroporation.

64. The method of claim 54 wherein the reverse transcriptase enzyme is introduced into the viable target cell.

65. The method of claim 54 wherein the reverse transcriptase enzyme is synthesized within the viable target cell.

66. The method of claim 54 wherein the reverse transcriptase enzyme and the polynucleotide molecule are introduced separately into the viable target cell.

67. The method of claim 54 wherein the reverse transcriptase enzyme and the polynucleotide molecule are concurrently introduced into the viable target cell.

68. The method of claim 67 wherein the step of introduction of the reverse transcriptase enzyme and the polynucleotide molecule is performed by electroporation.

69. The method of claim 54 wherein the viable target cells are eukaryotic cells.

* * * * *